(12) United States Patent
Chu et al.

(10) Patent No.: US 7,700,632 B2
(45) Date of Patent: Apr. 20, 2010

(54) BIARYLOXYMETHYLARENECARBOXYLIC ACIDS AS GLYCOGEN SYNTHASE ACTIVATOR

(75) Inventors: Chang An Chu, Mine Hill, NJ (US); Paul Gillespie, Westfield, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/970,620

(22) Filed: Jan. 8, 2008

(65) Prior Publication Data
US 2008/0108662 A1 May 8, 2008

Related U.S. Application Data

(62) Division of application No. 10/870,271, filed on Jun. 17, 2004, now Pat. No. 7,355,049.

(60) Provisional application No. 60/482,147, filed on Jun. 24, 2003, provisional application No. 60/569,356, filed on May 7, 2004.

(51) Int. Cl.
*A61K 31/44* (2006.01)
*C07D 211/70* (2006.01)
*C07D 211/78* (2006.01)

(52) U.S. Cl. .................. 514/344; 514/345; 514/352; 514/357; 546/286; 546/289; 546/290; 546/329

(58) Field of Classification Search .......... 546/286, 546/289, 290, 329, 330, 339; 514/344, 345, 514/352, 357
See application file for complete search history.

(56) References Cited

FOREIGN PATENT DOCUMENTS

| DE | 28 42 243 | 4/1980 |
|---|---|---|
| DE | 4142514 | 6/1993 |
| WO | WO 93/24442 | 12/1993 |
| WO | WO 97/39748 A1 | 10/1997 |
| WO | WO 97/40017 | 10/1997 |
| WO | WO 2004/012656 | 2/2004 |
| WO | WO 2004/058679 A2 | 7/2004 |
| WO | WO 2004/067524 A1 | 8/2004 |

OTHER PUBLICATIONS

Hajduk, PH. J. et al., *J. Med. Chem.*, (2002) 45(26) 5628-5639.

*Primary Examiner*—Janet L. Andres
*Assistant Examiner*—Raymond Covington
(74) *Attorney, Agent, or Firm*—George W. Johnston; Patricia S. Rocha-Tramaloni

(57) ABSTRACT

The present invention relates to compounds of formula (I)

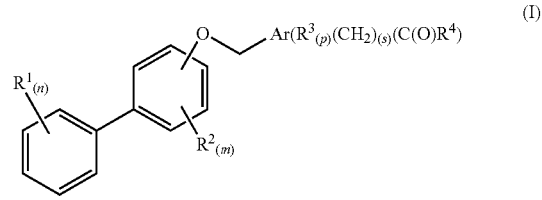

wherein $R^1$, $R^2$, $R^3$, $R^4$, m, n, p and s are as defined in the description and claims, and pharmaceutically acceptable salts thereof. The compounds are useful for the treatment and/or prophylaxis of diseases that are associated with the activation of the glycogen synthase enzyme, such as diabetes.

18 Claims, No Drawings

BIARYLOXYMETHYLARENECARBOXYLIC ACIDS AS GLYCOGEN SYNTHASE ACTIVATOR

PRIORITY TO RELATED APPLICATION(S)

This application is a division of U.S. application Ser. No. 10/870,271, filed Jun. 17, 2004, now pending, which claims the benefit of U.S. Provisional Application Ser. Nos. 60/480,900 filed Jun. 24, 2003; 60/482,147 filed Jun. 24, 2003 and 60/569,356, filed May 7, 2004. The entire contents of the above-identified applications are hereby incorporated by reference.

BACKGROUND OF THE INVENTION

The present invention is concerned with novel biaryloxymethylarenecarboxylic acids and their pharmaceutically acceptable salts, their manufacture and their use as medicaments. The present invention further relates to pharmaceutical compositions containing these compounds.

Diabetes mellitus is a common and serious disorder, affecting 10 million people in the U.S. [Harris, M. I. *Diabetes Care* 1998 21 (3S) *Supplement,* 11C], putting them at increased risk of stroke, heart disease, kidney damage, blindness, and amputation. Diabetes is characterized by decreased insulin secretion and/or an impaired ability of peripheral tissues to respond to insulin, resulting in increased plasma glucose levels. The incidence of diabetes is increasing, and the increase has been associated with increasing obesity and a sedentary life. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. However, these factors are often unable to control the disease, and there are a number of drug treatments available, including insulin, metformin, sulfonylureas, acarbose, and thiazolidinediones. Each of these treatments has disadvantages and there is an ongoing need for new drugs to treat diabetes.

Metformin is an effective agent that reduces fasting plasma glucose levels and enhances the insulin sensitivity of peripheral tissue, mainly through an increase in glycogen synthesis [De Fronzo, R. A. *Drugs* 1999, 58 *Suppl.* 1, 29]. Metformin also leads to reductions in the levels of LDL cholesterol and triglycerides [Inzucchi, S. E. *JAMA* 2002, 287, 360]. However, it loses its effectiveness over a period of years [Turner, R. C. et al. *JAMA* 1999, 281, 2005].

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. *Expert Opin. Investig. Drugs* 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. *JAMA* 2002, 287, 360] and, like metformin, they lose efficacy over time [Turner, R. C. et al. *JAMA* 1999, 281, 2005]. A further problem often encountered in patients treated with sulfonylureas is hypoglycemia [Salas, M. and Caro, J. J. *Adv. Drug React. Tox. Rev.* 2002, 21, 205-217].

Acarbose is an inhibitor of the enzyme alpha-glucosidase which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. *JAMA* 2002, 287, 360].

Because none of these treatments is effective over the long term without serious side effects, there is a need for new drugs for the treatment of type 2 diabetes.

In skeletal muscle and liver, there are two major pathways of glucose utilization: glycolysis, or oxidative metabolism, where glucose is oxidized to pyruvate; and glycogenesis, or glucose storage, where glucose is stored in the polymeric form glycogen. The key step in the synthesis of glycogen is the addition of the glucose derivative UDP-glucose to the growing glycogen chain, and this step is catalyzed by the enzyme glycogen synthase [Cid, E. et al. *J. Biol. Chem.* 2000, 275, 33614]. There are two isoforms of glycogen synthase, found in liver [Bai, G. et al. *J. Biol. Chem.* 1990, 265, 7843] and in other peripheral tissues including muscle [Browner, M. F. et al. *Proc. Nat. Acad. Sci. U.S.A.* 1989, 86, 1443]. There is clinical and genetic evidence implicating glycogen synthase in type 2 diabetes. Both basal and insulin-stimulated glycogen synthase activity in muscle cells from diabetic subjects were significantly lower than in cells from lean non-diabetic subjects [Henry, R. R. et al. *J. Clin. Invest.* 1996, 98, 1231-1236; Nikoulina, S. E. et al. *J. Clin. Enocrinol. Metab.* 2001, 86, 4307-4314]. Furthermore, several studies have shown that levels of glycogen are lower in diabetic patients than in control subjects [Eriksson, J. et al. *N. Engl. J. Med.* 1989, 331, 337; Schulman, R. G. et al. *N. Engl. J. Med.* 1990, 332, 223; Thorburn, A. W. et al. *J. Clin. Invest.* 1991, 87, 489], and in addition, genetic studies have shown associations in several populations between type 2 diabetes and mutation in the GYS1 gene encoding the muscle isoform of glycogen synthase [Orhu-Melander, M. et al. *Diabetes* 1999, 48, 918].

Glycogen synthase is subject to complex regulation, involving phosphorylation at least nine sites [Lawrence J. C., Jr. and Roach, P. J. *Diabetes* 1997, 46, 541]. The dephosphorylated form of the enzyme is active. Glycogen synthase is phosphorylated by a number of enzymes of which glycogen synthase kinase 3β (GSK3β) is the best understood [Tadayyon, M. and Smith, S. A. *Expert Opin. Investig. Drugs* 2003, 12, 307], and glycogen synthase is dephosphorylated by protein phosphatase type I (PP1) and protein phosphatase type 2A (PP2A). In addition, glycogen synthase is regulated by an endogenous ligand, glucose-6-phosphate which allosterically stimulates the activity of glycogen synthase by causing a change in the conformation of the enzyme that renders it more susceptible to dephosphorylation by the protein phosphatases to the active form of the enzyme [Gomis, R. R. et al. *J. Biol. Chem.* 2002, 277, 23246].

Several mechanisms have been proposed for the effect of insulin in reducing blood glucose levels, each resulting in an increase in the storage of glucose as glycogen. First, glucose uptake is increased through recruitment of the glucose transporter GLUT4 to the plasma membrane [Holman, G. D. and Kasuga, M. *Diabetologia* 1997, 40, 991]. Second, there is an increase in the concentration of glucose-6-phosphate, the allosteric activator of glycogen synthase [Villar-Palasi, C. and Guinovart, J. J. *FASEB J.* 1997, 11, 544]. Third, a kinase cascade beginning with the tyrosine kinase activity of the insulin receptor results in the phosphorylation and inactivation of GSK31, thereby preventing the deactivation of glycogen synthase [Cohen, P. *Biochem. Soc. Trans.* 1993, 21, 555; Yeaman, S. J. *Biochem. Soc. Trans.* 2001, 29, 537].

Because a significant decrease in the activity of glycogen synthase has been found in diabetic patients, and because of its key role in glucose utilization, the activation of the enzyme glycogen synthase holds therapeutic promise for the treatment of type 2 diabetes. The only known allosteric activators of the enzyme are glucose-6-phosphate [Leloir, L. F. et al. *Arch. Biochem. Biophys.* 1959, 81, 508] and glucosamine-6-phosphate [Virkamaki, A. and Yki-Jarvinen, H. *Diabetes* 1999, 48, 1101].

SUMMARY OF THE INVENTION

Briefly stated, novel biaryloxymethylarenecarboxylic acids have been found to be glycogen synthase activators. Consequently, the compounds of the present invention are useful for the treatment and/or prophylaxis of type 2 diabetes, and/or impaired glucose tolerance, as well as other conditions wherein the activation of the glycogen synthase enzyme gives a therapeutic benefit.

Some biaryloxymethylarenecarboxylic acids are known in the art. However, none of these known compounds have been associated with either the treatment of diseases mediated by the activation of the glycogen synthase enzyme or to any pharmaceutical composition for the treatment of diseases mediated by the activation of the glycogen synthase enzyme. Andersen, H. S. et al. WO 9740017 discloses the structure and synthetic route to 3-(biphenyl-4-yloxymethyl)-benzoic acid as an intermediate in the synthesis of SH2 inhibitors. Winkelmann, E. et al. DE 2842243 discloses 5-(biphenyl-4-yloxymethyl)-thiophene-2-carboxylic acid as a hypolipemic agent. Mueller, T. et al. DE 4142514 discloses 2-(biphenyl-3-yloxymethyl)-benzoic acid as a fungicide.

The following compounds are commercially available from ChemBridge Corporation, San Diego, Calif. or ChemDiv, Inc. San Diego, Calif. They have no reported utility.

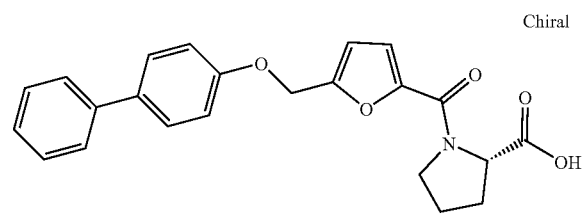

S-1-[5-(Biphenyl-4-yloxymethyl)-furan-2-carbonyl]-pyrrolidine-2carboxylic acid

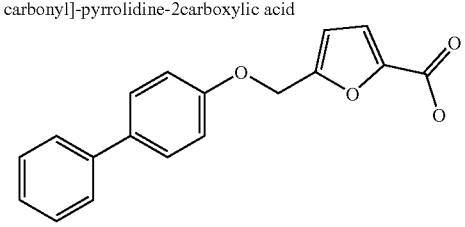

5-(Biphenyl-4-yloxymethyl)-furan-2-carboxylic acid

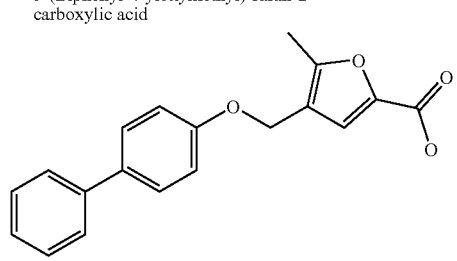

4-(Biphenyl-4-yloxymethyl)-5-methyl-furan-2-carboxylic acid

-continued

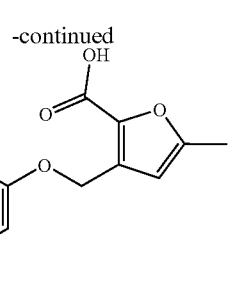

3-(Biphenyl-4-yloxymethyl)-5-methyl-furan-2-carboxylic acid

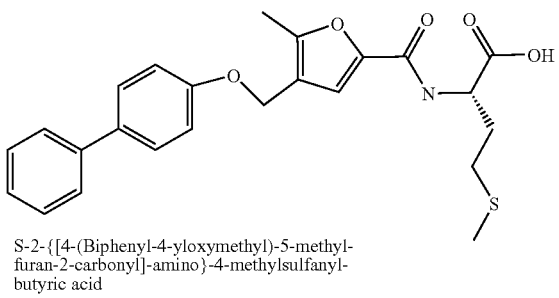

S-2-{[4-(Biphenyl-4-yloxymethyl)-5-methyl-furan-2-carbonyl]-amino}-4-methylsulfanyl-butyric acid

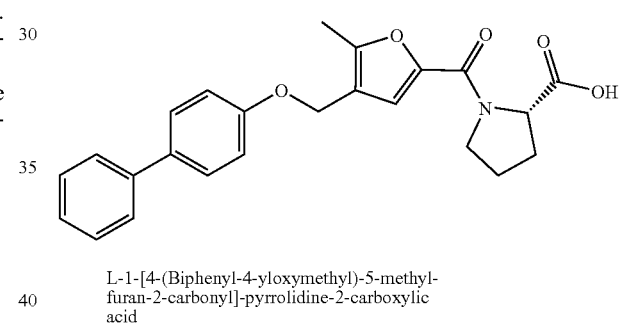

L-1-[4-(Biphenyl-4-yloxymethyl)-5-methyl-furan-2-carbonyl]-pyrrolidine-2-carboxylic acid According to one aspect of the present invention, there is provided a compound of formula (I)

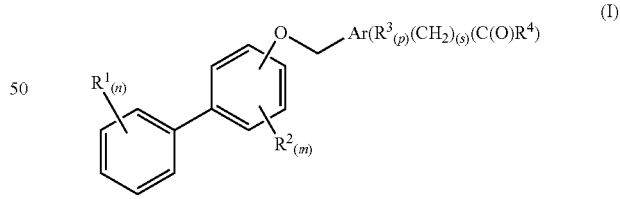

wherein $R^1$, $R^2$, $R^3$, $R^4$ n m, p and s are as defined below.

According to another aspect of the present invention, there is provided a pharmaceutical composition comprising a compound of formula (I) together with the prior art compounds disclosed above which have shown pharmaceutical activity, or pharmaceutically acceptable salts thereof and a pharmaceutically acceptable carrier and/or adjuvant.

According to a further aspect of the present invention there is provided a method for treating or preventing diseases which are associated with activation of the glycogen synthase enzyme, comprising administering to a patient in need thereof, a therapeutically effective amount of a compound of formula (I) together with the above disclosed prior art compounds.

These and other features, aspects and advantages of the present invention will become better understood with reference to the following description and claims.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven preferably of one to four carbon atom(s).

The term "halogen" refers to fluorine, chlorine, bromine and iodine, preferably to fluorine and chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Alkyl groups can optionally be substituted e.g. with halogen, hydroxy, lower-alkoxy, lower-alkoxy-carbonyl, $NH_2$, N(H, lower-alkyl) and/or N(lower-alkyl)$_2$. Unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl". Unsubstituted lower-alkyl groups are preferred.

The term "alkoxy" refers to the group R'—O—, wherein R' is alkyl. The term "lowers alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Alkoxy and lower-alkoxy groups may optionally have a substitution pattern as described earlier in connection with the term "alkyl". Unsubstituted alkoxy and lower-alkoxy groups are preferred.

The term "amino acid" refers to both natural amino acids, to their enantiomers, and to unnatural amino acids. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenyalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, allo-isoleucine, N-methylglycine, N-methylisoleucine, N-methylvaline, norvaline, norleucine, ornithine and pipecolic acid.

The term "aryl" relates to an aromatic carbocyclic or heterocyclic ring or ring system, preferably having from 5 to 6 carbon atoms. Examples of aryl groups include phenyl, furanyl, thiophenyl, pyridinyl, thiazolyl and oxazolyl, which can optionally be mono- or multiply-substituted by lower-alkyl, lower-alkoxy, halogen, CN, $CF_3$, hydroxy, $NO_2$, $NH_2$, N(H, lower-alkyl) and/or N(lower-alkyl)$_2$. Preferred substituents are lower-alkyl, lower-alkoxy, halogen, and/or $NO_2$.

The term "heterocycle" refers to a 5- or 6-membered ring which can comprise 1, 2 or 3 atoms selected from nitrogen, oxygen and/or sulfur such as tetrahydropyridine, dihydrofuran, dihydropyran, furyl, pyrrolyl, pyridyl, 1,2-, 1,3- and 1,4-diazinyl, thienyl, oxazolyl, oxadiazolyl, isoxazolyl, thiazolyl, isothiazolyl or imidazolyl. A heterocycle group may be optionally substituted with an aryl group or have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulfuric acid, phosphoric acid, citric acid, formic acid, maleic acid, acetic acid, fumaric acid, succinic acid, tartaric acid, methanesulfonic acid, p-toluenesulfonic acid and the like, which are non toxic to living organisms. Preferred salts with acids are formates, maleates, citrates, hydrochlorides, hydrobromides and methanesulfonic acid salts.

This term also encompasses carboxylate salts having organic and inorganic cations, such as alkali and alkaline earth metal cations (for example, lithium, sodium, potassium, magnesium, barium and calcium), ammonium; or organic cations, for example, dibenzylammonium, benzylammonium, 2-hydroxyethylammonium, bis(2-hydroxyethyl) ammonium, phenylethylbenzylammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term "leaving group" relates to a group which is removed or replaced during a reaction. Examples of leaving groups are halogen, mesylate and tosylate.

In detail, the present invention relates to compounds of formula (I)

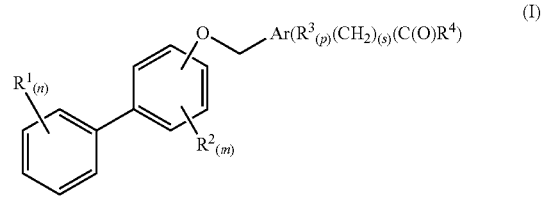

wherein

Ar is an aromatic carbocyclic or heterocyclic ring;

$R^1$, $R^2$ and $R^3$ are independently selected from the group consisting of lower alkyl lower alkoxy, trifluoromethyl, halogen, hydroxy, amino, alkylamino, dialkylamino, cyano and nitro;

$R^4$ is hydroxy or an amino acid attached through a nitrogen atom of the amino acid;

n is 0, 1, 2, 3, 4 or 5;

m is 0, 1, 2, 3 or 4;

p is 0, 1 or 2, and s is 0, 1 or 2 or a pharmaceutically acceptable salt thereof, provided that a) when Ar is furanyl, p and s are zero, the compound is not either S-1-[5-(biphenyl-4-yloxymethyl)-furan-2-carbonyl]-pyrrolidine-2-carboxylic acid or 5-(biphenyl-4-yloxymethyl)-furan-2-carboxylic acid, b) when Ar is phenyl, the compound is not either 3-(biphenyl-4-yloxymethyl)-benzoic acid or 2-(biphenyl-3-yloxymethyl)-benzoic acid, and c) when Ar is thiophenyl, the compound is not 5-(biphenyl-4-yloxymethyl)-thiophene-2-carboxylic acid.

In a preferred embodiment, the present invention relates to compounds of formula (I), wherein $R^1$, $R^2$ and $R^3$ are hydrogen atoms.

In another preferred embodiment, the present invention relates to compounds of formula (I) as defined above, in which $R^4$ is a hydroxyl group.

In addition, compounds of formula (I) as defined above, wherein $R^4$ is a proline, attached through its nitrogen atom, represent another preferred embodiment of the present invention.

Compounds of formula (I), wherein Ar is an aryl, preferably a phenyl group, represent another preferred embodiment of the present invention.

Another preferred embodiment of the present invention relates to compounds of formula (I) as defined above, wherein Ar is furanyl.

Still another preferred embodiment of the present invention relates to compounds of formula (I) as defined above, wherein Ar is thiophenyl.

Yet another preferred embodiment of the present invention relates to compounds of formula (I) as defined above, wherein Ar is thiazolyl.

Compounds of formula (I) represent a preferred embodiment of the present invention and pharmaceutically acceptable salts of compounds of formula (I) individually also represent a preferred embodiment of the present invention.

Preferred compounds of general formula (I) are those selected from the group consisting of
3-(3-Chloro-biphenyl-4-yloxymethyl)-benzoic acid;
3-(Biphenyl-3-yloxymethyl)-benzoic acid;
3-(4'-Methyl-biphenyl-4-yloxymethyl)-benzoic acid;
3-(4'-Bromo-biphenyl-4-yloxymethyl)-benzoic acid;
3-(4'-Chloro-biphenyl-4-yloxymethyl)-benzoic acid;
3-(2'-Nitro-biphenyl-4-yloxymethyl)-benzoic acid;
3-(4'-Methoxy-biphenyl-4-yloxymethyl)-benzoic acid;
5-(3-Chloro-biphenyl-4-yloxymethyl)-furan-2-carboxylic acid;
5-(Biphenyl-3-yloxymethyl)-furan-2-carboxylic acid;
5-(4'-Methyl-biphenyl-4-yloxymethyl)-furan-2-carboxylic acid;
5-(4'-Bromo-biphenyl-4-yloxymethyl)-furan-2-carboxylic acid;
5-(4'-Chloro-biphenyl-4-yloxymethyl)-furan-2-carboxylic acid;
5-(2'-Nitro-biphenyl-4-yloxymethyl)-furan-2-carboxylic acid;
5-(4'-Nitro-biphenyl-4-yloxymethyl)-furan-2-carboxylic acid;
2-(3-Chloro-biphenyl-4-yloxymethyl)-benzoic acid;
2-(4'-Methyl-biphenyl-4-yloxymethyl)-benzoic acid;
2-(2'-Nitro-biphenyl-4-yloxymethyl)-benzoic acid;
2-(Biphenyl-4-yloxymethyl)-benzoic acid;
5-(2'-Nitro-biphenyl-4-yloxymethyl)-thiophene-2-carboxylic acid;
6-(2'-Nitro-biphenyl-4-yloxymethyl)-pyridine-2-carboxylic acid;
6-(Biphenyl-4-yloxymethyl)-pyridine-2-carboxylic acid;
2-(3-Chloro-biphenyl-4-yloxymethyl)-thiazole-4-carboxylic acid;
2-(Biphenyl-3-yloxymethyl)-thiazole-4-carboxylic acid;
2-(4'-Methyl-biphenyl-4-yloxymethyl)-thiazole-4-carboxylic acid;
2-(4'-Bromo-biphenyl-4-yloxymethyl)-thiazole-4-carboxylic acid;
2-(4'-chloro-biphenyl-4-yloxymethyl)-thiazole-4-carboxylic acid;
2-(2'-Nitro-biphenyl-4-yloxymethyl)-thiazole-4-carboxylic acid;
2-(4'-Methoxy-biphenyl-4-yloxymethyl)-thiazole-4-carboxylic acid;
2-(Biphenyl-4-yloxymethyl)-thiazole-4-carboxylic acid;
4-(4'-Chloro-biphenyl-4-yloxymethyl)-thiazole-2-carboxylic acid;
4-(Biphenyl-4-yloxymethyl)-thiazole-2-carboxylic acid;
1-[5-(Biphenyl-4-yloxymethyl)-furan-2-carbonyl]-D-pyrrolidine-2-carboxylic acid;
(rac)-1-[5-(Biphenyl-4-yloxymethyl)-furan-2-carbonyl]-piperidine-2-carboxylic acid; and
1-{[5-(Biphenyl-4-yloxymethyl)-furan-2-carbonyl]-amino}-cyclopentanecarboxylic acid.

It will be appreciated, that the compounds of general formula (I) in this invention may be derivatized at functional groups to provide derivatives which are capable of conversion back to the parent compound in vivo.

As described above, the compounds of formula (I) of the present invention along with the disclosed prior art compounds in the above table i.e. compounds of the formula

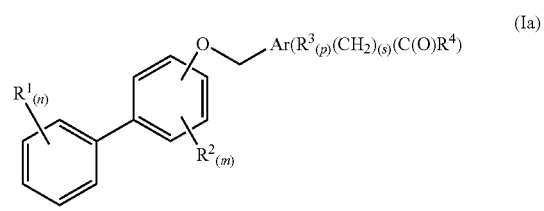

(Ia)

wherein $R^1$, $R^2$, $R^3$, $R^4$, Ar, m, n, p and s are as above may be used as medicaments for the treatment and/or prophylaxis of diseases mediated by the activation of the glycogen synthase enzyme. Preferably, the compounds of the present invention may be used to treat type 2 diabetes.

The invention therefore also relates to pharmaceutical compositions comprising a compound of formula Ia and a pharmaceutically acceptable carrier and/or adjuvant.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The compounds of formula I and Ia and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) and Ia can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 4 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

General Synthesis of Compounds According to the Invention

The compounds of the present invention can be prepared by any conventional means. Suitable processes for synthesizing these compounds are provided in the examples. Generally, compounds of formula I can be prepared according to one of the synthetic routes described below: Nucleophilic Displacement or Suzuki Coupling. The sources of the starting materials for these reactions are described subsequently.

Nucleophilic Displacement

As shown in Scheme 1, compounds of the invention can be prepared by nucleophilic displacement of a leaving group LG from a compound of formula 5 by a hydroxybiaryl of formula 4 to form a compound of formula 6 in which R1 represents a protective group commonly used for the protection of a carboxylic acid. The protective group is then cleaved to give the compound of the invention of formula 1.

Many protective groups R1 are known to those of skill in the art of organic synthesis. For example, several suitable protective groups are enumerated in "Protective Groups in Organic Synthesis" [Greene. T. W. and Wuts, P. G. M., $2^{nd}$ Edition, John Wiley & Sons, N.Y. 1991]. Preferred protective groups are those compatible with the reaction conditions used to prepare compounds of the invention. Examples of such protective groups are lower alkyl straight-chain or branched esters (e.g., methyl (R1=$CH_3$), ethyl (R1=$CH_2CH_3$), or tert-butyl (R1=$C(CH_3)_3$) esters), or the benzyl ester (R1=$CH_2C_6H_5$).

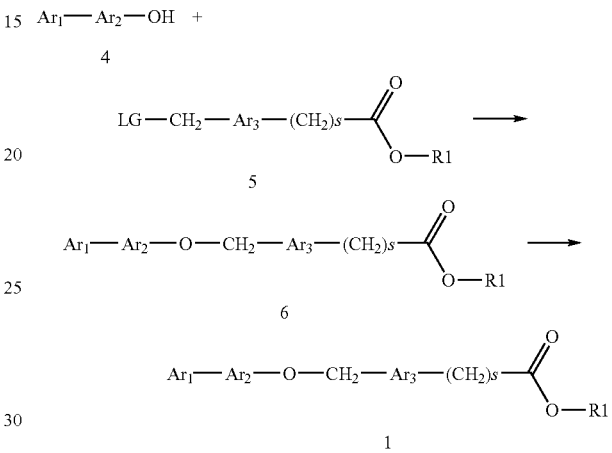

Scheme 1

The nucleophilic displacement of the leaving group LG in compound 5 can be effected by any conventional means. For example, in the case where LG represents the leaving group chlorine, bromine, or iodine, the reaction can conveniently be carried out by treating compound 6 with compound 4 in the presence of a base such as an alkali metal hydride (for example, sodium hydride) or an alkali metal carbonate (for example, potassium carbonate) in an inert solvent (e.g., N,N-dimethylformamide) at a temperature between about room temperature and about 100 degrees.

The conversion of compound 6, in which R1 represents a protective group commonly used for the protection of a carboxylic acid, to compound 1 by deprotection of the carboxylic acid protective group is carried out using reaction conditions that are well known in the field of organic synthesis, and many of which are outlined in "Protective Groups in Organic Synthesis" [Greene, T. W. and Wuts, P. G. M., $2^{nd}$ Edition, John Wiley & Sons, N.Y. 1991]. For example, in the case where R1 is methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature. As another example, in the case where R1 is a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature. As a final (but not limiting) example, in the case where R1 is a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

Suzuki Coupling

As shown in Scheme 2, compounds of the invention can be prepared by a reaction sequence starting with nucleophilic displacement of a leaving group LG from a compound of formula 5 by a compound of formula 7, in which X represents a group that can act as a leaving group in a noble metal-catalyzed coupling reaction such as a Suzuki reaction or a Stille reaction, to form a compound of formula 9 in which R1 represents a protective group commonly used for the protection of a carboxylic acid. The compound of formula 9 can then be reacted with an organometallic reagent of formula 10 (for example, a boronic acid or an organotin reagent) under noble metal catalysis to give a biaryl compound of formula 6. The protective group is then cleaved to give the compound of the invention of formula 1.

Many protective groups R1 are known to those of skill in the art of organic synthesis. For example several suitable protective groups are enumerated in "Protective Groups in Organic Synthesis" [Greene, T. W. and Wuts, P. G. M., $2^{nd}$ Edition, John Wiley & Sons N.Y. 1991]. Preferred protective groups are those compatible with the reaction conditions used to prepare compounds of the invention. Examples of such protective groups are lower alkyl straight-chain or branched esters (e.g. methyl (R1=$CH_3$), ethyl (R1=$CH_2CH_3$), or tert-butyl (R1=$C(CH_3)_3$) esters), or the benzyl ester (R1$CH_2C_6H_5$).

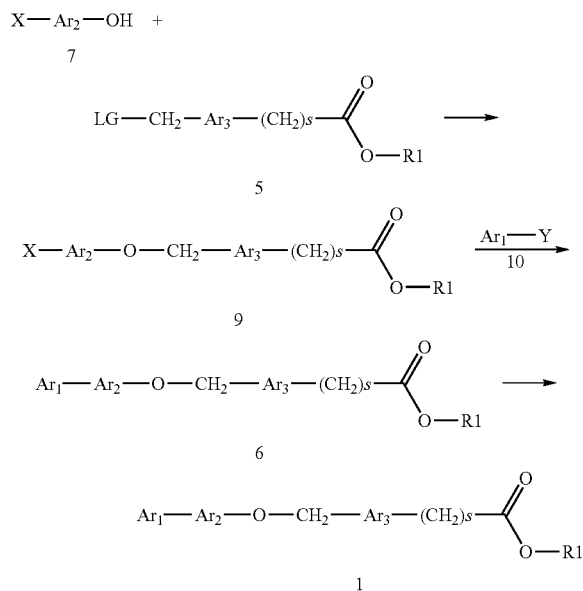

Scheme 2

The nucleophilic displacement of the leaving group LG in compound 5 can be effected by any conventional means. For example, in the case where LG represents the leaving group chlorine, bromine, or iodine, the reaction can conveniently be carried out by treating compound 5 with compound 7 in the presence of a base such as an alkali metal hydride (for example, sodium hydride) or an alkali metal carbonate (for example, potassium carbonate) in an inert solvent (e.g., N,N-dimethylformamide) at a temperature between about room temperature and about 100 degrees.

The reaction of a compound of formula 9, where X represents a leaving group such as iodine, bromine, or triflate, with a compound of formula 10, where Y represents boronic acid, boronate ester, trimethyltin or tri-n-butyl-tin, to give a compound of formula 6 can be effected using Suzuki or Stille coupling conditions which are well known to one of average skill in the art. For example, the reaction can be conveniently carried out by reacting a compound of formula 9 where X represents iodine with a compound of formula 10 where Y represents $B(OH)_2$, in a convenient inert solvent such as a polar aprotic solvent (e.g., N,N-dimethylformamide) or an ether (e.g. dioxane) or water, in the presence of a catalytic amount of a palladium(0) complex (e.g., tetrakis(triphenylphosphine)palladium(0)) or a compound which can be reduced in situ to give palladium(0) (for example, palladium (II) acetate or bis(triphenylphosphine)palladium(II) chloride), in the optional additional presence of a catalytic amount of a phosphine ligand, for example tri-o-tolylphosphine or tri-tert-butylphosphine, and also in the presence of an inorganic base, for example, an alkali metal carbonate, bicarbonate or phosphate (e.g. potassium phosphate or sodium carbonate) at a temperature between about room temperature and about 100 degrees, and preferably at between about room temperature and about 50 degrees.

The conversion of compound 6, in which R1 represents a protective group commonly used for the protection of a carboxylic acid, to compound 1 by deprotection of the carboxylic acid protective group is carried out using reaction conditions that are well known in the field of organic synthesis, and many of which are outlined in "Protective Groups in Organic Synthesis" [Greene, T. W. and Wuts, P. G. M., $2^{nd}$ Edition, John Wiley & Sons, N.Y. 1991]. For example, in the case where R1 is methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature. As another example, in the case where R1 is a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature. As a final (but not limiting) example, in the case where R1 is a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

Starting Materials: Compounds of Formula 4

Many compounds of formula 4 are known compounds and can be synthesized according to literature procedures. Some examples are included in the table.

| Name | Reference |
|---|---|
| 3-Allyl-biphenyl-4-ol | White et al. J. Amer. Chem. Soc. 1958, 80, 3271 |
| 4'-Bromo-biphenyl-4-ol | Bell et al. J. Chem. Soc. 1927, 1131 |
| 2-(4-Bromo-phenyl)-pyrimidin-5-ol | Kizner, T. A. et al. Khim. Geterotsikl. Soedin. 1990, 801 |
| 4'-Butoxy-biphenyl-4-ol | Pollino, Joel M. Synthesis 2002, 1277 |
| 3-tert-Butyl-biphenyl-4-ol | Davis B. R. et al. J. Chem. Soc. Perkin Trans. 1 1982, 1499 |
| 5-(4-tert-Butyl-phenyl)-thiophen-3-ol | Hunter, G. A. et al. J. Chem. Soc. Perkin Trans. 1 1995, 1209 |
| 2-Chloro-biphenyl-4-ol | Mattingly, P. G. et al. U.S. Pat. No. 5,145,790 |
| 3-Chloro-biphenyl-4-ol | Burckhalter et al. J. Am. Chem. Soc. 1946, 68, 1894 |
| 4'-Chloro-biphenyl-4-ol | Abernethy et al. J. Am. Chem. Soc. 1943, 65, 1464 |
| 2',5'-Dichloro-biphenyl-4-ol | Reich, I. L. et al. J. Org. Chem. 1981, 46, 3721 |
| 3,4'-Dichloro-biphenyl-4-ol | Abernethy et al. J. Am. Chem. Soc. 1943, 65, 1464 |
| 3,5-Dichloro-biphenyl-4-ol | Colbert et al. J. Am. Chem. Soc. 1934, 56, 2128 |
| 3,2'-Diethyl-biphenyl-4-ol | Schroetter, E. et al. Pharmazie 1974, 29, 374 |
| 2',4'-Difluoro-biphenyl-4-ol | Hannah, J. et al. J. Med. Chem. 1978, 21, 1093 |
| 4'-Ethyl-biphenyl-4-ol | Leigh, T. et al. GB 1121722 |
| 4'-Fluoro-biphenyl-4-ol | Takatsu, H. et al. Mol. Cryst. Liq. Cryst. 1984, 108, 157 |
| 4'-Fluoro-3-methyl-biphenyl-4-ol | Hannah, J. et al. J. Med. Chem. 1978, 21, 1093 |
| 6-(4-Fluoro-phenyl)-pyridin-3-ol | Walford, G. L. et al. J. Med. Chem. 1971, 14, 339 |
| 4'-Hydroxy-biphenyl-4-carbaldehyde | Revell, J. D. Org. Lett. 2002, 4, 3071 |
| 1-(4'-Hydroxy-biphenyl-4-yl)-ethanone | Boy, P. J. Org. Chem. 1994, 59, 4482 |
| 4'-Iodo-biphenyl-4-ol | Angeletti et al. Gazz. Chim. Ital. 1928, 58, 634 |
| 4'-Methoxy-biphenyl-4-ol | Sakurai, H. et al. J. Org. Chem. 2002, 67, 2721 |
| 5-(4-Methoxy-phenyl)-thiophen-3-ol | Pinkin, L. D. et al. Chem. Heterocycl. Compd. (Engl. Transl.) 1987, 23, 345 |
| 3-Methyl-biphenyl-4-ol | Colbert et al. J. Am. Chem. Soc. 1946, 68, 270 |
| 4'-Methyl-biphenyl-4-ol | Colbert et al. J. Am. Chem. Soc. 1946, 68, 270 |
| 2'-Nitro-biphenyl-4-ol | Schultz et al. Justus Liebigs Ann. Chem. 1881, 209, 351 |
| 3-Nitro-biphenyl-4-ol | Behre. H. WO 0177061 |
| 4'-Nitro-biphenyl-4-ol | Bell et al. J. Chem. Soc. 1926, 3047 |
| 2-(4-Nitro-phenyl)-pyrimidin-5-ol | Kizner, T. A. et al. Khim. Geterotsikl. Soedin. 1990, 801 |
| 6-Phenyl-pyridin-3-ol | Kurita, J. Chem. Pharm. Bull. 1987, 35, 3166 |
| 2-Phenyl-pyrimidin-5-ol | Maurer, F. et al. U.S. Pat. No. 5,010,193 |
| 5-Phenyl-thiophen-3-ol | Friedlaender et al. Chem. Ber. 1912, 45, 3391 |
| 3,5,4'-Trichloro-biphenyl-4-ol | Abernethy et al. J. Am. Chem. Soc. 1943, 65, 1464 |
| 4'-Trifluoromethyl-biphenyl-4-ol | Le Barny, P. et al. Mol. Cryst. Liq. Cryst. 1985, 127, 413 |
| 2',4',6'-Trimethyl-biphenyl-4-ol | Haefelinger, G. et al. Chem. Ber. 1978, 111, 1323 |

In addition, many compounds of formula 4 are commercially available, including the following:

| Name | Supplier |
|---|---|
| 2-Amino-4-phenylphenol | Aldrich, Milwaukee, WI |
| 2-Bromo-4-phenylphenol | Maybridge plc, Tintagel, UK |
| 4-Chloro-4'-hydroxybiphenyl | TCI America, Portland, OR |
| 4,4'-Dihydroxybiphenyl | Aldrich, Milwaukee, WI |
| 3,4'-Dimethyl-biphenyl-4-ol | Maybridge plc, Tintagel, UK |
| 2-Fluoro-biphenyl-4-ol | Bionet Research Ltd. Cornwall, UK |
| 4-Fluoro-4'-hydroxy biphenyl | Apin Chemicals Ltd., Abingdon, Oxon, UK |
| 4-Hydroxy-2'-nitrobiphenyl | TCI America, Portland, OR |

| Name | Supplier |
|---|---|
| 4-Hydroxy-4'-aminobiphenyl | Apin Chemicals Ltd., Abingdon, Oxon, UK |
| 4'-Hydroxy-4-biphenylcarbonitrile | Aldrich, Milwaukee, WI |
| 4'-Hydroxy-4-biphenylcarboxylic acid | Aldrich, Milwaukee, WI |
| 4-Hydroxy-4'-methoxybiphenyl | TCI America, Portland, OR |
| 4-Hydroxy-4'-nitrobiphenyl | TCI America, Portland, OR |
| 2-Iodo-4-phenylphenol | SALOR, Aldrich, Milwaukee, WI |
| 4-(4'-Iodophenyl)phenol | Apin Chemicals Ltd., Abingdon, Oxfordshire, UK |
| 4-(4-Methylphenyl)phenol | Maybridge plc, Tintagel, UK |
| 4'-Hydroxy-biphenyl-4-carboxylic acid methyl ester | Bionet Research Ltd., Cornwall, UK |
| 2-Nitro-4-phenylphenol | Lancaster Synthesis Ltd., Lancashire, UK |
| 4-Phenylphenol | Aldrich, Milwaukee, WI |

Compounds of formula 4 that are not known in the literature may be prepared using reactions that are known per se. For example, they may be conveniently prepared according to Scheme 3.

Scheme 3

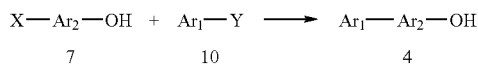

The reaction of a compound of formula 7, where X represents a leaving group such as iodine, bromine, chlorine, or triflate, with a compound of formula 10, where Y represents boronic acid, boronate ester, trimethyltin or tri-n-butyl-tin, to give a compound of formula 6 can be effected using Suzuki or Stille coupling conditions which are well known to one of average skill in the art. For example, the reaction can be conveniently carried out by reacting a compound of formula 7 where X represents iodine with a compound of formula 10 where Y represents $B(OH)_2$, in a convenient inert solvent such as a polar aprotic solvent (e.g., N,N-dimethylformamide) or an ether (e.g., dioxane) or water in the presence of a catalytic amount of a palladium(0) complex (e.g., tetrakis(triphenylphosphine)palladium(0)) or a compound which can be reduced in situ to give palladium(0) (for example, palladium (II) acetate or bis(triphenylphosphine)palladium(II) chloride), in the optional additional presence of a catalytic amount of a phosphine ligand, for example tri-o-tolylphosphine or tri-tert-butylphosphine, and also in the presence of an inorganic base, for example, an alkali metal carbonate, bicarbonate or phosphate (e.g., potassium phosphate or sodium carbonate) at a temperature between about room temperature and about 100 degrees, and preferably at between about room temperature and about 50 degrees. As further examples, the reaction can be run according to the conditions of Sakurai, H. et al. *J. Org. Chem.* 2002, 67, 2721, or the reaction can be run on solid phase using the conditions of Revell, J. D. and Ganesan, A. *Org. Lett.* 2002, 4, 3071.

Starting Materials: Compounds of Formula 5

Many compounds of formula 5, in which R1 represents a protective group commonly used for the protection of a carboxylic acid, are known compounds and can be synthesized according to literature procedures. Some examples are included in the table.

| Name | Reference |
|---|---|
| 3-(Bromomethyl)-phenyl-acetic acid benzyl ester | A. Dorville et al., J. Med. Chem. 1992, 35, 2551 |
| 4-(Bromomethyl)-phenyl-acetic acid benzyl ester | K. Shen et al., J. Biol. Chem. 2001, 276, 47311 |
| 2-(Bromomethyl)-phenyl-acetic acid tert-butyl ester | C. L. Newton et al., WO 2003011222 |
| 2-(Bromomethyl)-phenyl-acetic acid ethyl ester | A. Peyman et al. U.S. Pat. No. 5,242,908 |
| 3-(Bromomethyl)-phenyl-acetic acid ethyl ester | S. R. Kasibhatla et al. J. Med. Chem. 2000, 43, 1508 |
| 2-(Bromomethyl)-phenyl-acetic acid methyl ester | J. S. Sawyer et al., J. Med. Chem. 1992, 35, 1200 |
| 2-(Bromomethyl)-phenyl-acetic acid methyl ester | F. Roussi et al., Tetrahedron 1998, 54, 10363 |
| 3-(Bromomethyl)-phenyl-acetic acid methyl ester | J. H. Musser et al. J. Med. Chem. 1987, 30, 96 |
| 4-(Bromomethyl)-phenyl-acetic acid methyl ester | K. C. Santhosh et al. J. Med. Chem. 2001, 44, 703 |
| 3-[3-(Bromomethyl)phenyl]-propanoic acid, tert-butyl ester | A. G. Caldwell and N. Whittaker, U.S. Pat. No. 4,204,068 |
| 3-[4-(Bromomethyl)phenyl]-propanoic acid, ethyl ester | M. Babej et al., DE 2331081 |
| 3-[3-(Bromomethyl)phenyl]-propanoic acid, methyl ester | N. A. Norman, U.S. Pat. No. 4,084,058 |
| 3-[4-(Bromomethyl)phenyl]-propanoic acid, methyl ester | D. V. Patel et al. WO 9623813 |

-continued

| Name | Reference |
|---|---|
| 4-(Bromomethyl)-1H-1,2,3-triazole-1-acetic acid, ethyl ester | F. Palacios et al., Org. Prep. Proc. Intl. 1995, 27, 603 |
| 2-Bromomethyl-benzoic acid tert-butyl ester | Ziegler, T. et al. Tetrahedron Lett. 2001, 42, 569-572 |
| 3-Bromomethyl-benzoic acid tert-butyl ester | Danho, W. et al. U.S. Pat. No. 5,508,437 |
| 2-Bromomethyl-benzoic acid methyl ester | Dvornikovs, V. et al. J. Org. Chem. 2002, 67, 2160-2167 |
| 3-Bromomethyl-benzoic acid methyl ester | Dvornikovs, V. et al. J. Org. Chem. 2002, 67, 2160-2167 |
| 5-Bromomethyl-2-furancarboxylic acid ethyl ester | Tsuboi, S. et al. Bull. Chem. Soc. Japan 1987, 60, 1807-1812 |
| 5-Bromomethyl-2-furancarboxylic acid methyl ester | Wityak, J. et al. Bioorg. Med. Chem. Lett. 1995, 5, 2097-2100 |
| 6-Bromomethyl-pyridine-2-carboxylic acid methyl ester | Scopes, D. I. C. et al. J. Med. Chem. 1992, 35, 490-501 |
| 2-Bromomethyl-thiazole-4-carboxylic acid ethyl ester | Hallinan, E. A. et al. Bioorg. Med. Chem. 2001, 9, 1-6 |
| 5-Bromomethyl-thiophene-2-carboxylic acid methyl ester | Curtin, M. L. et al. J. Med. Chem. 1998, 41, 74-95 |
| 3-Chloromethyl-benzoic acid benzyl ester | Chen, D.-W. et al. J. Chem. Soc. Perkin Trans. 1 2001, 2796-2803 |
| 2-Chloromethyl-benzoic acid ethyl ester | Gadient, F. et al. Helv. Chim. Acta 1962, 45, 1860-1870 |
| 3-Chloromethyl-benzoic acid methyl ester | Matsukawa, T. et al. Yakugaku Zasshi 1950, 70, 535-537. Chem. Abs. 45: 36092 (1951) |
| 4-(Chloromethyl)-2-furanacetic acid, ethyl ester | K.-T. Tang et al. Bull. Korean Chem. Soc. 2002, 23, 1333 |
| 5-Chloromethyl-2-furancarboxylic acid n-butyl ester | Bremner, J. G. M. et al. U.S. Pat. No. 2,450,108 |
| 5-Chloromethyl-2-furancarboxylic acid ethyl ester | Chakraborty, T. K. et al. Tetrahedron Lett. 2002, 43, 1317-1320 |
| 4-(Chloromethyl)-2-furanpropanoic acid, methyl ester | J. S. U and K. T. Kang, Bull. Korean Chem. Soc. 1994, 15, 1019 |
| 5-(Chloromethyl)-2-furanpropanoic acid, methyl ester | J. W. Patterson and J. H. Fried, U.S. Pat. No. 3,922,289 |
| 4-(Chloromethyl)-1H-imidazole-1-acetic acid, 2-propenyl ester, monohydrochloride | V. M. Girijavallabhan et al., J. Antibiot. 1986, 39, 1182 |
| 2-(Chloromethyl)-5-methyl-4-oxazoleacetic acid, methyl ester | S. Shibata et al., WO 9401433 |
| 5-(Chloromethyl)-2-methyl-3-thiopheneacetic acid, methyl ester | M. C. Van Zandt and L. Geraci, Leo. WO 2003044015 |
| 3-(3-Chloromethyl-1,2,4-oxadiazol-5-yl)propionic acid, methyl ester | G. Beaton et al., WO 2003015785 |
| 4-(Chloromethyl)-2-oxazolepropanoic acid, ethyl ester | Y. Momose et al., WO 9803505 |
| 2-(Chloromethyl)-phenyl-acetic acid methyl ester | K. Hirai et al., WO 9700850 |
| 4-(Chloromethyl)-phenyl-acetic acid methyl ester | S. H. Park et al. EP 889020 |
| 3-[4-(Chloromethyl)phenyl]-propanoic acid, ethyl ester | T. Mase et al. EP 214732 |
| 3-[4-(Chloromethyl)phenyl]-propanoic acid, 1-methylethyl ester | Y. Fukuda et al. WO 9747581 |
| 6-Chloromethyl-pyridine-2-carboxylic acid ethyl ester | Fornasier, R. et al. J. Chem. Soc. Perkin Trans. 2 1986, 233-238 |
| 6-(Chloromethyl)-3-pyridinepropanoic acid, ethyl ester | T. H. Brown, EP 39989 |
| 5-Chloromethyl-thiophene-2-carboxylic acid methyl ester | Kozmik, V. et al. Collect. Czech. Chem. Commun. 1992, 57, 1483-1486 |
| 4-(Chloromethyl)-2-thiopheneacetic acid, ethyl ester | K.-T. Tang et al. Bull. Korean Chem. Soc. 2002, 23, 1333 |
| 4-(Chloromethyl)-2-thiopheneacetic acid, methyl ester | M. C. Van Zandt and L. Geraci, Leo. WO 2003044015 |

-continued

| Name | Reference |
|---|---|
| 4-(Chloromethyl)-2-thiophenepropanoic acid, methyl ester | K. T. Kang and J. S. U, Synth. Commun. 1995, 25, 2647 |
| 5-(Chloromethyl)-2-thiophenepropanoic acid, methyl ester | J. W. Patterson and J. H. Fried, U.S. Pat. No. 3,922,289 |
| 3-Iodomethyl-benzoic acid methyl ester | Fuson, R. C. et al. J. Am. Chem. Soc. 1940, 62, 1180-1183 |
| 4-(Iodomethyl)-2-furanacetic acid, ethyl ester | K.-T. Tang et al. Bull. Korean Chem. Soc. 2002, 23, 1333 |
| 5-Iodomethyl-2-furancarboxylic acid allyl ester | Greenspan, P. D. et al. J. Med. Chem. 2001, 44, 4524-4534 |
| 4-(Iodomethyl)-2-thiopheneacetic acid, ethyl ester | K.-T. Tang et al. Bull. Korean Chem. Soc. 2002, 23, 1333 |
| 5-Methanesulfonyloxymethyl-furan-2-carboxylic acid ethyl ester | Summers, J. B., Jr. et al. U.S. Pat. No. 5,486,525 |

In addition, some compounds of formula 5 are commercially available, including the following:

| Name | Supplier |
|---|---|
| 6-Bromomethyl-pyridine-2-carboxylic acid methyl ester | ChemPacific, Baltimore, MD |
| 5-Chloromethyl-2-furancarboxylic acid ethyl ester | Aldrich, Milwaukee, WI |
| 5-Chloromethyl-2-furancarboxylic acid methyl ester | Aldrich, Milwaukee, WI |
| 2-Bromomethyl-benzoic acid ethyl ester | Pfaltz & Bauer, Inc., Waterbury, CT |
| 2-Bromomethyl-benzoic acid methyl ester | ChemPacific, Baltimore, MD |
| 3-Bromomethyl-benzoic acid methyl ester | Lancaster Synthesis Ltd., Lancashire, UK |

Compounds of formula 5 that are neither known in the literature nor commercially available may be conveniently prepared by reactions that are well known in the field of organic synthesis, and these reactions can be represented generically as in Scheme 4.

Scheme 4

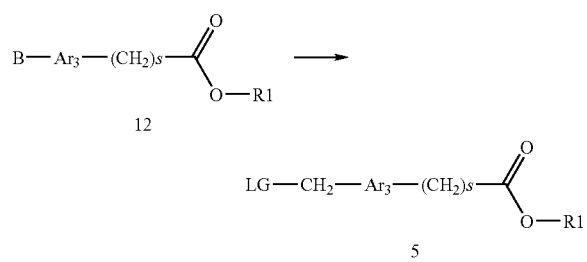

Three examples of reactions represented by Scheme 4 are described below. As will be clear to one of average skill in the art, not all reactions can be used to prepare all compounds of formula 5, but reactions appropriate for the preparation of specific compounds of formula 5 will be apparent to a synthetic organic chemist.

For example, a compound of formula 5, where LG represents chlorine, can be prepared from a compound of formula 12 where B represents hydrogen by an electrophilic aromatic substitution reaction by treating the compound of formula 12 where B represents hydrogen with formaldehyde and hydrogen chloride, in the presence of a Lewis acid catalyst, preferably zinc chloride, in a suitable inert solvent, for example, a halogenated alkane (such as methylene chloride, chloroform, 1,2-dichloroethane, or the like) at a temperature between about room temperature and the boiling point of the solvent, preferably at about 35 degrees celsius. Clearly this reaction is limited to cases where the compound of formula 12 is susceptible to electrophilic aromatic substitution at the desired point of attachment, and further, to cases where the compound of formula 5 is stable to mineral acids and to Lewis acids. Examples of compounds of formula 5 which fulfill these criteria will be known to one of average skill in the art. An example of such a reaction can be found in Moldenhauer, O. et al. Justus Liebigs Ann. Chem. 1953, 580, 176.

Compounds of formula 5 where LG represents bromine can be prepared by treating a compound of formula 12 where B represents $CH_3$ with N-bromosuccinimide or 3,3-dimethyl-N,N'-dibromohydantoin in an inert solvent such as a halogenated alkane (for example, carbon tetrachloride) or acetonitrile, in the optional addition presence of a catalyst such as azobis(isobutyronitrile) or benzoyl peroxide at a suitable temperature, conveniently at the boiling point of the solvent, and in the optional additional presence of a source of light; or by treating a compound of formula 12 where B represents $CH_3$ with bromine in an inert solvent such as a mixture of water and an aromatic hydrocarbon (e.g., benzene) or a halogenated alkane (e.g., chloroform) under irradiation with an incandescent light. Compounds of formula 5 where LG represents chlorine can be prepared by treating a compound of formula 12 where B represents $CH_3$ with N-chlorosuccinimide or sulfuryl chloride in an inert solvent such as a halogenated alkane (for example, carbon tetrachloride) or acetonitrile in the optional additional presence of a catalyst such as azobis(isobutyronitrile) or benzoyl peroxide at a suitable temperature, conveniently at the boiling point of the solvent, and in the optional additional presence of a source of light; or by treating a compound of formula 12 where B represents $CH_3$ with chlorine in an inert solvent such as a mixture of water and an aromatic hydrocarbon (e.g., benzene) or a halogenated alkane (e.g., chloroform or carbon tetrachloride) under irradiation with an incandescent light.

A compound of formula 5 where LG represents bromine can be prepared by treating a compound of formula 12 where B represents $CH_2OH$ with phosphorus tribromide or a mixture of N-bromosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 5 where LG represents chlorine can be prepared by treating a compound of formula 12 where B represents $CH_2OH$ with thionyl chloride or a mixture of N-chlorosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 5 where LG represents $OSO_2E$ where E represents lower alkyl or aryl can be prepared by treating a compound of formula 12 where B represents $CH_2OH$ with a sulfonyl chloride $ESO_2Cl$ (for example, methanesulfonyl chloride or p-toluenesulfonyl chloride) in the presence of a base such as a tertiary amine (e.g., triethylamine or diethylisopropylamine) in an inert solvent such as a halogenated hydrocarbon (e.g., methylene chloride) at a temperature between about 0 degrees and about room temperature, preferably at about 0 degrees. A compound of formula 5 where LG represents iodine can be prepared by treating a compound of formula 5 where LG represents chlorine, bromine, or $OSO_2E$ where E represents lower alkyl or aryl, with an alkali metal iodide (e.g., sodium iodide) in an inert solvent such as a ketone (e.g., acetone or methyl ethyl ketone) at a temperature between about 50 degrees and about 80 degrees, conveniently at about the boiling point of the solvent.

Starting Materials: Compounds of Formula 7

Many compounds of formula 7, where X represents a leaving group such as chlorine, iodine, bromine, or triflate, are known compounds and can be synthesized according to literature procedures. Some examples are included in the table.

In addition, many compounds of formula 7 are commercially available, including the following:

| Name | Supplier |
| --- | --- |
| 4-Bromo-2-chloro-phenol | Aldrich, Milwaukee, WI |
| 4-Bromo-2-chloro-6-methyl-phenol | Lancaster Synthesis Ltd., Lancashire, UK |
| 5-Bromo-2,3-difluoro-phenol | Lancaster Synthesis Ltd., Lancashire, UK |
| 4-Bromo-3,5-dimethyl-phenol | Aldrich, Milwaukee, WI |
| 5-Bromo-2-hydroxy-benzamide | SALOR, Aldrich, Milwaukee, WI |
| 5-Bromo-2-hydroxy-benzonitrile | Oakwood Products, West Columbia, SC |
| 5-Bromo-2-hydroxy-3-nitro-pyridine | Oakwood Products, West Columbia, SC |
| 3-Bromo-5-hydroxy-pyridine | Specs and Biospecs, Rijswijk, Netherlands |
| 4-Bromo-phenol | Aldrich, Milwaukee, WI |
| 2-Chloro-3-fluoro-5-hydroxy-pyridine | Asymchem International, Inc., Durham, NC |
| 5-Chloro-2-hydroxy-4,6-dimethyl-nicotinonitrile | Maybridge plc, Tintagel, UK |
| 2-Chloro-5-hydroxy-pyridine | Asymchem International, Inc., Durham, NC |
| 2-Hydroxy-5-bromo-pyrimidine | Lancaster Synthesis Ltd., Lancashire, UK |
| 4-Iodo-2-methyl-phenol | Aldrich, Milwaukee, WI |
| 3-Iodo-phenol | Aldrich, Milwaukee, WI |
| 4-Iodo-phenol | Aldrich, Milwaukee, WI |

Compounds of formula 7 that are neither known in the literature nor commercially available may be conveniently prepared by reactions that are well known in the field of organic synthesis as shown in Scheme 5.

| Name | Reference |
| --- | --- |
| 3-Bromo-4-chloro-phenol | Liedholm, B. Acta Chem. Scand Series B 1984, B38, 877-894 |
| 4-Bromo-2-chloro-phenol | Jaeger, R. et al. U.S. Pat. No. 4,223,166 |
| 6-Bromo-5-chloro-pyridin-3-ol | Koch, V. et al. Synthesis 1990, 499-501 |
| 4-Bromo-2,6-dichlorophenol | Malm, J. et al. WO 02/62780 |
| 5-Bromo-2-hydroxy-benzene-sulfonamide | Meyer, W. et al. U.S. Pat. No. 4,479,821 |
| 4-Bromo-3-nitro-phenol | Lavoie, E. J. et al. U.S. Pat. No. 6,486,167 |
| 3-Bromo-4-methyl-phenol | Jacquesy, J. C. J. Chem. Soc. Chem. Commun. 1980, 110-111 |
| 5-Bromo-2-nitro-phenol | Makosza, M. et al. J. Org. Chem. 1998, 63, 4199-4208 |
| 3-Bromo-phenol | Matarasso-Tchiroukhine, E. Ann. Chim. (Paris) 1958, 3, 405-459 Chem. Abs. 53: 34694 |
| 2-tert-Butyl-4-iodophenol | Tashiro, M. et al. J. Org. Chem. 1977, 42, 835-838 |
| 3,5-Dimethyl-4-iodophenol | Lu, Y. et al. Synthesis 2001, 1639-1644 |
| 3-Iodo-phenol | Noelting and Stricker Chem. Ber. 1887, 20, 3019 |
| 5-Bromo-2-hydroxy-thiazole-4-carboxylic acid ethyl ester | Serra, G. et al. Heterocycles 1995, 41, 2701-2712 |
| 5-Bromo-3-hydroxy-thiophene-2-carbonitrile | Binder, D. et al. Arch. Pharm. (Weinheim) 1988, 321, 391-395 |
| 6-Bromo-pyridin-2-ol | Wibaut, J. P. et al. Recl. Trav. Chim. Pays-Bas 1940, 59, 202-206 |
| 6-Bromo-pyridin-3-ol | den Hertog, H. J. et al. Recl. Trav. Chim. Pays-Bas 1950, 69, 1281-1288 |
| 2-Chloro-4,6-dimethyl-pyrimidinol | Hurst, D. T. Heterocycles 1984, 22, 79-84 |
| 2-Chloro-4-methoxy-6-methyl-pyrimidin-5-ol | Dohmori, R. et al. Chem. Pharm. Bull. 1970, 18, 1908-1914 |
| 2-Chloro-pyrimidin-5-ol | Hurst, D. T. et al. J. Chem. Soc. 1965, 7116-7119 |
| 6-Iodo-pyridin-3-ol | Edgar, K. J. et al. J. Org. Chem. 1990, 55, 5287-5291 |

Scheme 5

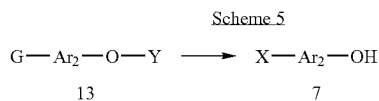

A compound of formula 7 can be prepared from a compound of formula 13 where G and X represent the same substituent selected from among chlorine, bromine, and iodine, and Y represents methyl using reactions that are well known in the field of organic synthesis. Several of these methods are outlined in "Protective Groups in Organic Synthesis" (Greene, T. W. and Wuts, P. G. M., $2^{nd}$ Edition, John Wiley & Sons, N.Y. 1991). For example, a compound of formula 7 can be formed by treating with trimethylsilyliodide a compound of formula 13 where G and X represent the same substituent selected from among chlorine, bromine, and iodine, and Y represents methyl. The reaction is conveniently carried out in an inert solvent, such as a halogenated alkane (e.g., chloroform) or acetonitrile, at a temperature between about room temperature and the boiling point of the solvent, preferably at about 50 degrees. Alternatively, a compound of formula 7 can be formed by heating a compound of formula 13 where G and X represent the same substituent selected from among chlorine, bromine, and iodine, and Y represents methyl with hydrogen bromide in acetic acid or water at reflux. As a third alternative, a compound of formula 7 can be formed by treating a compound of formula 13 where G and X represent the same substituent selected from among chlorine, bromine, and iodine, and Y represents methyl with boron tribromide in an inert solvent such as such as a halogenated alkane (e.g., chloroform or methylene chloride) at a temperature between about 0 degrees and about 40 degrees, conveniently at about room temperature.

A compound of formula 7 where X represents chlorine and the position of attachment of X is para to the hydroxy group can be prepared by treating a compound of formula 13 where G represents hydrogen and Y represents hydrogen with sulfuryl chloride in an inert solvent such as ether or a halogenated hydrocarbon (e.g. chloroform), at a temperature between about 0 degrees and about 35 degrees, preferably at about room temperature. A compound of formula 7 where X represents bromine and the position of attachment of X is para to the hydroxy group can be prepared by treating a compound of formula 13 where G represents hydrogen and Y represents hydrogen with bromine in an inert solvent such as water, or carbon tetrachloride, or acetic acid, at a temperature between about 0 degrees and about room temperature, preferably at about room temperature. Alternatively, the same compound 7 where X represents bromine and the position of attachment of X is para to the hydroxy group can be prepared by treating a compound of formula 13 where G represents hydrogen and Y represents hydrogen with a tribromide salt (e.g., tetrabutylammonium tribromide or benzyltrimethylammonium tribromide) in an inert solvent such as a halogenated hydrocarbon (e.g. methylene chloride or chloroform) at a temperature between about 0 degrees and about room temperature, preferably at about room temperature. A compound of formula 7 where X represents iodine and the position of attachment of X is para to the hydroxy group can be prepared by treating a compound of formula 13 where G represents hydrogen and Y represents hydrogen with iodine, or iodine monochloride in an inert solvent such as water, in the presence of an inorganic base such as an alkali metal hydroxide (e.g., sodium hydroxide) or an alkali metal carbonate (e.g., sodium carbonate) at a temperature between about 0 degrees and about room temperature, preferably at about room temperature. The same compound of formula 7 where X represents iodine and the position of attachment of X is para to the hydroxy group can be prepared by treating a compound of formula 13 where G represents hydrogen and Y represents hydrogen with sodium iodide and sodium hypochlorite in an inert solvent such as a mixture of water and an alcohol (e.g., methanol), at a temperature close to 0 degrees. This last reaction and several alternatives are described in Edgar, K. J. and Falling, S. N. *J. Org. Chem.* 1990, 55, 5287-5291.

A compound of formula 7 where X represents chlorine, bromine, or iodine can be prepared by treating a compound of formula 13 where G represents NH2 and Y represents hydrogen using the Sandmeyer reaction which is well known in the art of organic synthesis. Details of this reaction can be found in Hodgson, H. H. *Chem. Rev.* 1947, 40, 251-277 and also in Nonhebel, D. C., Copper-catalyzed Single-electron Oxidations and Reductions, Special Publication—Chemical Society (London) 1970, 24, 409-437 ISSN: 0577-618X. For example, a compound of formula 13 where G represents NH2 and Y represents hydrogen can be converted to a diazonium intermediate of formula 13 where G represents $N_2^+$ and Y represents hydrogen by treatment with sodium nitrite in the presence of a mineral acid (for example, hydrochloric acid or sulfuric acid) in water at a temperature between about −10 degrees and about 10 degrees, preferably about zero degrees. Without isolation, this diazonium intermediate can then be converted to a compound of formula 7 where X represents chlorine by treatment with copper(I) chloride, to a compound of formula 7 where X represents bromine by treatment with copper(I) bromide, or to a compound of formula 7 where X represents iodine by treatment with potassium iodide.

Starting Materials: Compounds of Formula 10

Many compounds of formula 10, where Y represents boronic acid, boronate ester, trimethyltin or tri-n-butyl-tin, are known compounds and can be synthesized according to literature procedures. Some examples are included in the table.

| Name | Reference |
|---|---|
| 4-Acetyl-3-fluorophenyl-boronic acid | Holmes-Farley, S. R. et al. US 2003064963 |
| (5-tert-Butoxy-furan-2-yl)-trimethyl-stannane | Pearce, B. C. Syn. Commun. 1992, 22, 1627-1643. |
| 4-n-Butyl-phenyl-boronic acid | Glende, C. et al. Mutation Res. 2002, 515, 15-38 |
| (5-Cyano-2-thienyl)-boronic acid | Fensome, A. et al. U.S. Pat. No. 6,355,648 |
| 4-[(Diethylamino)carbonyl]phenyl-boronic acid | Gravel, M. et al. J. Org. Chem 2002, 67, 3-15 |

-continued

| Name | Reference |
| --- | --- |
| 3,5-Dimethoxy-4-methylphenyl-boronic acid | Ishiwata, H. et al. US 2003027814 |
| 2-(2,6-Dimethyl-phenyl)-4,4,5,5-tetramethyl-[1,3,2]dioxaborolane | Baudoin, O. et al. J. Org. Chem. 2000, 65, 9268-9271 |
| Dimethyl-[4-(4,4,5,5-tetramethyl-[1,3,2]dioxaborolan-2-yl)-phenyl]-amine | Murata, M., J. Org. Chem. 1997, 62, 6458-6459 |
| 2,6-Dimethyl-4-(4,4,5,5-tetramethyl-[1,3,2]dioxaborolan-2-yl)-pyridine | Cho, J.-Y. et al. J. Am. Chem. Soc. 2000, 122, 12868-12869 |
| 2-(1-Ethoxyethyl)-phenyl-boronic acid | Dale, W. J. et al. J. Org. Chem. 1962, 27, 2598-2603 |
| 2-Ethoxy-5-tributylstannyl-thiazole | Wang, T. et al. WO 02/062423 |
| (5-Ethyl-furan-2-yl)-trimethyl-stannane | Sasabe, M. et al. Perkin 1 2000, 3786-3790 |
| 3-Hydroxy-phenyl-boronic acid | Bean, F. R. and Johnson. J. R. J. Am. Chem. Soc. 1932, 54, 4421 |
| 6-Methoxy-4-methyl-3-pyridinyl-boronic acid | Arvanitis, A. G. Bioorg. Med. Chem. Lett. 2003, 13, 289-291 |
| 2-Methoxy-phenyl-boronic acid | Rocca, P. et al Tetrahedron 1993, 49, 49-64 |
| 2-(4-Methoxy-phenyl)-4,4,5,5-tetramethyl-[1,3,2]dioxaborolane | Ishiyama, T. et al. Tetrahedron Lett. 1997, 38, 3447-3450 |
| (5-Methyl-furan-2-yl)-boronic acid | Florentin, D. et al. J. Heterocycl. Chem. 1976, 13, 1265-1272 |
| 2-Methyl-5-(trimethylstannyl)-thiazole | Wentland, M. P. et al. J. Med. Chem. 1993, 36, 1580-1596 |
| 2-Nitro-phenyl-boronic acid | Groziak, M. P. et al. J. Am. Chem. Soc. 1994, 116, 7597-7605 |
| 3-Pyridyl-boronic acid | Fischer, F. C. et al. Recl. Trav. Chim. Pays-Bas 1974, 93, 21-24 |
| 3-(4,4,5,5-Tetramethyl-[1,3,2]dioxaborolan-2-yl)-benzonitrile | Sebo, L. et al. Helv. Chim. Acta 2000, 83, 93-113 |
| 4-(4,4,5,5-Tetramethyl-[1,3,2]dioxaborolan-2-yl)-benzonitrile | Murata, M. J. Org. Chem. 1997, 62, 6458-6459 |
| 1-[4-(4,4,5,5-Tetramethyl-[1,3,2]dioxaborolan-2-yl)-phenyl]-ethanone | Fuerster, A. et al. Org. Lett. 2002, 4, 541-544 |
| 2-(4,4,5,5-Tetramethyl-1,3,2-dioxaborolan-2-yl)-thiazole | Marcuccio, S. et al. U.S. Pat. No. 6,399,779 |
| 4,4,5,5-Tetramethyl-2-(4-nitro-phenyl)-[1,3,2]dioxaborolane | Ishiyama, T. et al. Tetrahedron Lett. 1997, 38, 3447-3450 |
| 3-Thio-phenyl-boronic acid | Li, W. et al. J. Org. Chem. 2002, 67, 5394-5397 |

In addition, many compounds of formula 10, where Y represents boronic acid, boronate ester, trimethyltin or tri-n-butyl-tin, are commercially available, including the following:

| Name | Supplier |
| --- | --- |
| 3-Bromophenylboronic acid | Aldrich, Milwaukee, WI |
| 4-(2-Carboxyethyl)phenylboronic acid | Lancaster Synthesis Ltd., Lancashire, UK |
| 4-Carboxyphenylboronic acid | Aldrich, Milwaukee, WI |
| 2-Chlorophenylboronic acid | Aldrich, Milwaukee, WI |
| 4-Chlorophenylboronic acid | Aldrich, Milwaukee, WI |
| 3-Cyanophenylboronic acid | Aldrich, Milwaukee, WI |
| 2,6-Difluorophenylboronic acid | Aldrich, Milwaukee, WI |
| 3,5-Difluoro-(tri-n-butylstannyl)benzene | Maybridge plc, Tintagel, UK |
| 2,4-Dimethoxyphenylboronic acid | Aldrich, Milwaukee, WI |
| 2,5-Dimethoxyphenylboronic acid | Aldrich, Milwaukee, WI |
| 4-(Dimethylamino)phenylboronic acid | Aldrich, Milwaukee, WI |
| 4-Ethoxyphenylboronic acid | Aldrich, Milwaukee, WI |
| 2-Fluorobiphenyl-4-boronic acid | Lancaster Synthesis Ltd., Lancashire, UK |
| 3-Fluorophenylboronic acid | Aldrich, Milwaukee, WI |
| 4-Fluoro-2-methylphenylboronic acid | Lancaster Synthesis Ltd., Lancashire, UK |
| 4-Fluoro-(tri-n-butylstannyl)benzene | Maybridge plc, Tintagel, UK |
| 3-Formylfuran-2-boronic acid | Lancaster Synthesis Ltd., Lancashire, UK |
| Furan-2-boronic acid | Aldrich, Milwaukee, WI |
| 3-(Hydroxymethyl)phenylboronic acid | Aldrich, Milwaukee, WI |
| 4-(Hydroxymethyl)phenylboronic acid | Aldrich, Milwaukee, WI |
| 4-Iodophenylboronic acid | Aldrich, Milwaukee, WI |
| (3-Isopropylphenyl)boronic acid | Lancaster Synthesis Ltd., Lancashire, UK |
| (2-Methylphenyl)boronic acid | Aldrich, Milwaukee, WI |
| 3-Methylphenylboronic acid | Aldrich, Milwaukee, WI |
| 4-Methoxyphenylboronic acid | Aldrich, Milwaukee, WI |
| [(4-Methylsulfonyl)phenyl]boronic acid | Lancaster Synthesis Ltd., Lancashire, UK |

-continued

| Name | Supplier |
| --- | --- |
| 5-Methylthiophene-2-boronic acid | Aldrich, Milwaukee, WI |
| 2-Methyl(tri-n-butylstannyl)benzene | Maybridge plc, Tintagel, UK |
| 1-Naphthaleneboronic acid | Aldrich, Milwaukee, WI |
| 3-Nitrophenylboronic acid | Aldrich, Milwaukee, WI |
| 4-Phenoxyphenylboronic acid | Aldrich, Milwaukee, WI |
| 2-Thiopheneboronic acid | Aldrich, Milwaukee, WI |
| Thiophene-3-boronic acid | Aldrich, Milwaukee, WI |
| Tri-n-butyl(2-furyl)tin | Aldrich Chemical Company, Inc. |
| Tributyl(2-methoxyphenyl)stannane | Maybridge plc, Tintagel, UK |
| Tri-n-butyl(2-pyridyl)tin | Lancaster Synthesis Ltd. |
| 2-(Trifluoromethyl)phenylboronic acid | Aldrich, Milwaukee, WI |
| 3-(Trifluoromethoxy)phenylboronic acid | Aldrich, Milwaukee, WI |
| 3,4,5-Trifluorophenylboronic acid | Lancaster Synthesis Ltd., Lancashire, UK |
| 3,4,5-Trimethoxyphenylboronic acid | Lancaster Synthesis Ltd., Lancashire, UK |
| Trimethyl(phenyl)tin | Aldrich Chemical Company, Inc. |
| 3-(Tri-n-butylstannyl)pyridine | Maybridge plc, Tintagel, UK |
| Tri-n-butyl(2-thienyl)tin | Aldrich Chemical Company, Inc. |

Compounds of formula 10, where Y represents boronic acid, boronate ester, trimethyltin or tri-n-butyl-tin, that are neither known in the literature nor commercially available can be synthesized by procedures that are well known to one skilled in the art of organic synthesis. For example, a compound of this type can conveniently be synthesized according to Scheme 6 from a compound of formula 11, in which X represents bromine or iodine, by treatment with an alkyllithium (e.g., n-butyllithium) or magnesium (to form the Grignard reagent) in a suitable inert solvent such as an ether (such as tetrahydrofuran or diethyl ether) at a temperature appropriate for the reaction (for example, at approximately −78° C. for reaction with an alkyllithium, or at approximately room temperature for reaction with magnesium), followed by treatment with a trialkyl borate or trialkyltin chloride to form the compound of formula 10 where Y represents B(OH)$_2$ or trialkyltin, respectively.

Scheme 6

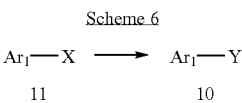

Additionally, the reaction can be carried out under noble metal catalysis. According to this route, the compound of formula 11 is conveniently reacted with a hexa-alkyl-distannane (such as hexamethyl-distannane or hexa-n-butyl-distannane) or 4,4,5,5-tetramethyl-[1,3,2]dioxaborolane or 4,4,5,5,4',4',5',5'-octamethyl-[2,2']bi[[1,3,2]dioxaborolanyl], in the presence of a noble metal catalyst (preferably a palladium catalyst such as tetrakis(triphenylphosphine)palladium(0) or palladium(II) chloride or palladium(II) acetate) and in the optional additional presence of a catalytic amount of a phosphine ligand, for example tri-o-tolylphosphine or tri-tert-butylphosphine. In the case of reaction with a hexa-alkyl-distannane, the reaction is optionally carried out in the presence of an organic base, for example, a tertiary amine (e.g., triethylamine), while in the case of reaction with a dioxaborolane, the reaction is carried out in the presence of an inorganic base (e.g., cesium fluoride, or potassium acetate, preferably potassium acetate). The reaction is conveniently carried out in an appropriate inert solvent such as a polar aprotic solvent (e.g., N,N-dimethylformamide, N,N-dimethylacetamide, dimethylsulfoxide, or acetonitrile) or an aromatic hydrocarbon (e.g., toluene) at a temperature between about room temperature and about 100 degrees, and preferably at between about room temperature and about 50 degrees. As additional examples, the specific reaction conditions utilized in the following publications can be followed, Baudoin, O. et al. J. Org. Chem. Soc. 2000, 65, 9268-9271; Ishiyama, T. et al. Tetrahedron Lett. 1997, 38, 3447-3450; Hylarides, M. D. J. Organomet. Chem. 1989, 367, 259-265; Read, M. W. et al. Org. Lett. 2000, 2, 3201-3204; Ishiyama, T. et al., Tetrahedron 1997, 57, 9813-9816, Fuerster, A. et al. Org. Lett. 2002, 4, 541-544.

Preparation of Compounds of the Invention where s Represents 2

In addition to the methods described above for the preparation of compounds of the invention, additional methods are available for the preparation of compounds of formula 1 in which s represents 2, as shown in Scheme 7. According to this process, compounds of formula 5B are converted to compounds of formula 15, either directly by nucleophilic displacement with a compound of formula 4, or by following a Suzuki coupling approach going through intermediate 9B. The nucleophilic displacement and Suzuki coupling reactions are analogous to those described above.

Scheme 7

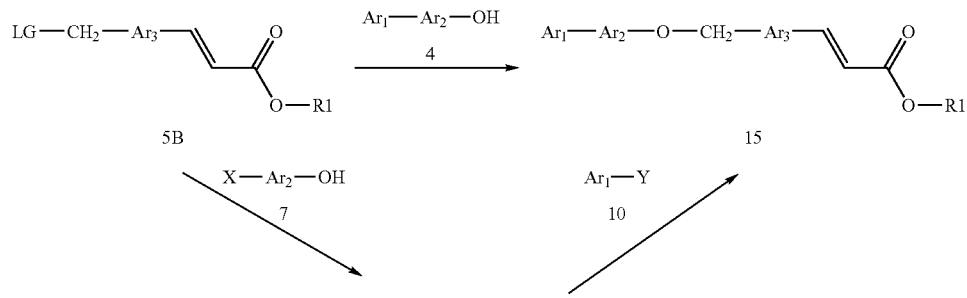

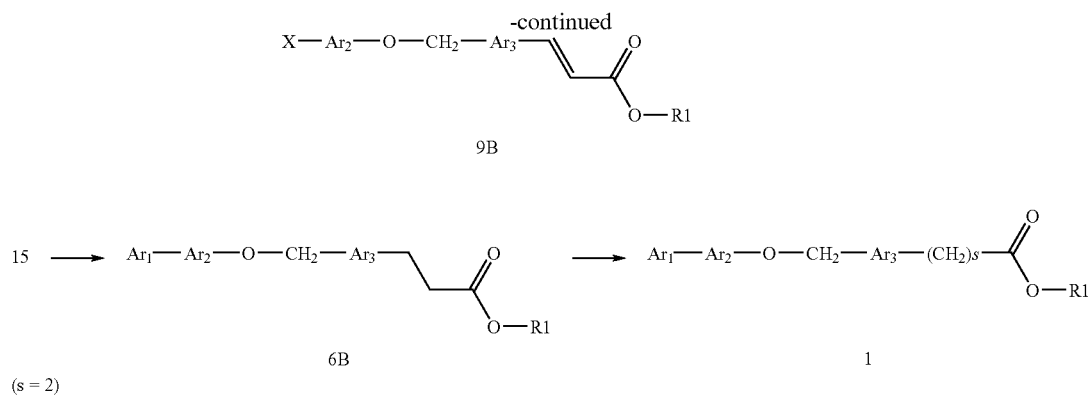

9B 6B
(s = 2)

1

Compounds of formula 15 can be converted to compounds of formula 6B by hydrogenation using a noble metal catalyst. This reaction may be carried out by treating the compound of formula 15 with hydrogen gas in the presence of a noble metal catalyst such as palladium-on-carbon in the presence of an inert solvent (for example, an alcohol such as ethanol) at about room temperature and under atmospheric pressure.

The compound of formula 6B can be converted to the compound of formula 1 where represents 2 by cleavage of the protective group R1. Conditions suitable for carrying out this reaction are described above for the conversion of a compound of formula 6 to a compound of formula 1.

Starting Materials Compounds of Formula 5B

Several compounds of formula 5B are known compounds and can be synthesized according to literature procedures. Examples are included in the table.

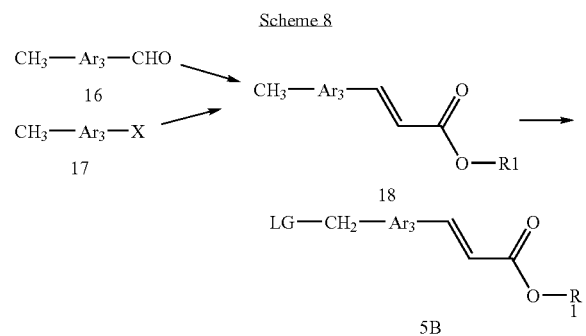

Scheme 8

A compound of formula 16 can be converted to a compound of formula 18 by reaction with a phosphorus ylide in a Wittig reaction, or with a phosphonate ester in a Horner-Wadsworth-Emmons reaction. Both of these reactions are well known to one of average skill in the art, and further information can be found for example in "Comprehensive Organic Transformations: A Guide to Functional Group

| | |
|---|---|
| (2E)-3-[2-(Bromomethyl)pheny]-2-propenoic acid, methyl ester | H. Juteau et al. Bioorg. Med. Chem. Lett. 2001, 11, 747 |
| (2E)-3-[2-(Bromomethyl)phenyl]-2-propenoic acid, tert-butyl ester | D. A. Price Synlett 1999, 1919 |
| (2E)-3-[3-(Bromomethyl)-2-pyridinyl]-2-propenoic acid, ethyl ester | Y. Gareau et al. WO 9947497 |
| (2E)-3-[4-(Bromomethyl)phenyl]-2-propenoic acid, methyl ester | P. L. Beaulieu et al. WO 2003010141 |
| (2E)-3-[4-(Chloromethyl)-5-methyl-2-oxazolyl]-2-propenoic acid, ethyl ester | Y. Momose et al., WO 2004024705 |
| (2E)-3-[4-(Chloromethyl)phenyl]-2-propenoic acid, ethyl ester | H. U. Blaser et al. EP 40177 |
| (2E)-3-[5-(Bromomethyl)-3-furanyl]-2-propenoic acid, methyl ester | L. M. Pevzner et al. Zhurnal Obshchei Khimii 1997, 67, 1710 |
| 3-[3-(Bromomethyl)phenyl]-2-propenoic acid, methyl ester | D. A. R. Happer J. Chem. Soc. Perkin Trans. 2 1983, 843 |
| 3-[3-(Chloromethyl)phenyl]-2-propenoic acid, methyl ester | D. A. R. Happer, J. Chem. Soc. Perkin Trans. 2 1983, 843 |
| 3-[4-(Bromomethyl)phenyl]-2-propenoic acid, methyl ester | H. Ohnishi et al. EP 501876 |
| 3-[4-(Bromomethyl)phenyl]-2-propenoic acid, methyl ester | D. V. Patel et al. WO 9623813 |
| 3-[4-(Chloromethyl)phenyl]-2-propenoic acid, methyl ester | D. A. R. Happer J. Chem. Soc. Perkin Trans. 2 1983, 843 |

Compounds of formula 5B that are not known in the literature may be prepared by any conventional means. For example, they may be conveniently prepared according to Scheme 8, starting from an aryl-carboxaldehyde of formula 16 or from a haloaromatic of formula 17.

Preparations" [R. C. Larock, VCH Publishers, Inc., N.Y. 1989, pages 173-184] and in "Advanced Organic Chemistry" [J. March, 3$^{rd}$ Edition, Wiley Interscience, NY, 1985]. For example, the compound of formula 16 can be treated with an alkyl(triphenylphosphoranylidene)-acetate, such as methyl (triphenylphosphoranylidene)acetate, in an inert solvent such as dichloromethane or tetrahydrofuran or benzene at a temperature around room temperature to give compound of formula 18. As a further example, the compound of formula 16 can be treated with a phosphonoacetate ester, such as triethyl phosphonacetate, in the presence of a base such as sodium hydride or cesium carbonate or potassium carbonate or sodium ethoxide, in an inert solvent such as N,N-dimethylformamide or dioxane or tetrahydrofuran at a temperature around room temperature to give the compound of formula 18.

A compound of formula 17 where X represents a group that can function as a leaving group in a noble metal-catalyzed coupling reaction such as a Heck reaction can be converted to a compound of formula 18 by reaction with an acrylate ester under nobel metal catalysis. For example, the reaction can be carried out by treating the compound of structure 17 with an acrylate ester, such as methyl acrylate or ethyl acrylate, in the presence of a source of palladium(0) such as palladium(II) acetate, in the optional presence of a phosphine such as triphenylphosphine or tri-ortho-tolylphosphine, preferably tri-ortho-tolylphosphine, in the presence of a base which may be an organic base (e.g., triethylamine) or an inorganic base (e.g, potassium carbonate, sodium hydrogen carbonate, thallium (I) acetate or silver acetate) in the optional additional presence of a phase-transfer catalyst such as tetra-n-butylammonium chloride, in an inert solvent (e.g., N,N-dimethylformamide or N,N-dimethylacetamide or acetonitrile) at a temperature between about room temperature and about 110 degrees, preferably at about 100 degrees.

The compound of formula 18 can be converted to a compound of formula 5b by treating it with a halogenating agent such as N-bromosuccinimide, in the presence of a catalytic amount of benzoyl peroxide or azobisisobutyronitrile (AIBN), in an inert solvent such as a halogenated hydrocarbon or a halocarbon such as carbon tetrachloride. The reaction is conveniently carried out at a temperature around the boiling point of the solvent or about 80 degrees whichever is lower.

The in vitro activation of glycogen synthase by compounds of the present invention can be demonstrated by means of the following test.

Twelve μl per well of substrate solution containing glycogen (4.32 mg/ml), 21.6 mM UDP-glucose, 21.6 mM phospho (enol)pyruvate and 2.7 mM NADH in 30 mM glycylglycine, pH 7.3 buffer is added into a polystyrene 384-well assay plate (BD Biosciences). Compound solution (8 μl/well) at various concentrations (0-57 μM) in 30 mM glycylglycine pH 7.3, 40 mM KCl, 20 mM MgCl2 plus 9.2% DMSO are added to the assay plate (columns 5-24). Enzyme solution (12 μl/well) containing glycogen synthase (16.88 μg/ml) pyruvate kinase (0.27 mg/ml), lactate dehydrogenase (0.27 mg/ml) in 50 mM Tris-HCl, pH 8.0, 27 mM DTT and bovine serum albumin (BSA, 0.2 mg/ml) is added to the assay plate (columns 3-24). As a blank control, enzyme solution without glycogen synthase is added into the top half wells of columns 1-2. To the bottom half wells of columns 1-2 are added a known activator, glucose 6-phosphate (18.9 mM) in addition to the enzyme solution. The reaction mixture is incubated at 37° C. The assay plate is then read for absorbance at 340 nm on a Tecan Ultra reader every 3 minutes up to a total of 30 minutes.

The enzyme activity (with or without compound) is calculated by the reaction rate and represented by the optical density change (ΔOD) per minute. Percent stimulation of glycogen synthase activity by a compound at various concentrations is calculated by the following formula:

% stimulation=100*Rs/Rt, where Rs is the reaction rate of the enzyme in the presence of compound and Rt is the reaction rate of the enzyme in the absence of compound.

SC2.0 is defined as the compound concentration that is needed to stimulate 200% of the enzyme activity.

The results obtained in the foregoing tests using representative compounds of structure 1 as the test compound are compiled in the following Table.

| Name | SC2.0 |
| --- | --- |
| 1-[5-(Biphenyl-4-yloxymethyl)-furan-2-carbonyl]-L-pyrrolidine-2-carboxylic acid | 1.4 μM |
| 1-{[5-(Biphenyl-4-yloxymethyl)-furan-2-carbonyl]-amino}-cyclopentanecarboxylic acid | 16.3 μM |
| 2-(3-Chloro-biphenyl-4-yloxymethyl)-benzoic acid | 10.3 μM |
| 2-(3-Chloro-biphenyl-4-yloxymethyl)-thiazole-4-carboxylic acid | 14.9 μM |
| 2-(4'-Chloro-biphenyl-4-yloxymethyl)-thiazole-4-carboxylic acid | 3.1 μM |
| 3-(4'-Bromo-biphenyl-4-yloxymethyl)-benzoic acid | 3.8 μM |
| 3-(4'-Methoxy-biphenyl-4-yloxymethyl)-benzoic acid | 9.6 μM |
| 5-(4'-Chloro-biphenyl-4-yloxymethyl)-furan-2-carboxylic acid | 0.8 μM |
| 5-(Biphenyl-3-yloxymethyl)-furan-2-carboxylic acid | 14.9 μM |
| 5-(Biphenyl-4-yloxymethyl)-thiophene-2-carboxylic acid | 12.7 μM |

EXAMPLES

The following examples illustrate preferred methods for synthesizing the compounds and formulations of the present invention.

Intermediate 1: 2-Bromomethyl-benzoic acid methyl ester

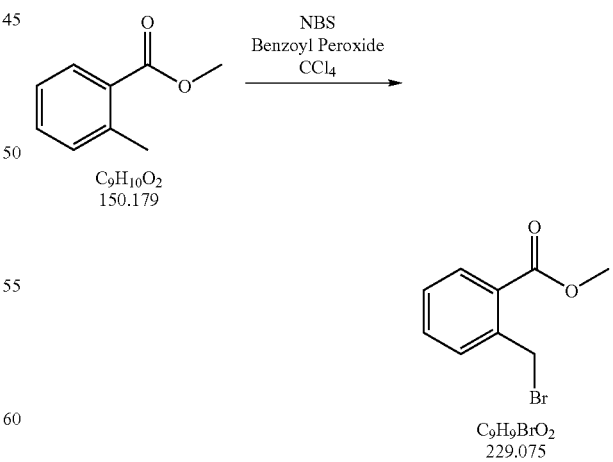

A mixture of methyl o-toluate (13.5 g, 89.9 mmol), NBS (17.6 g, 98.9 mmol), and benzoyl peroxide (50 mg, 0.2 mmol) in carbon tetrachloride (250 mL) was heated at reflux over the weekend. The reaction mixture was allowed to cool, and it was then filtered. The solvents were evaporated under reduced pressure and the residue was purified by chromatography, eluting with 3% ethyl acetate/hexanes to give 2-bromomethyl-benzoic acid methyl ester (7.7 g, 37%) as a white solid. ¹HNMR (CDCl₃): δ 7.97 (dd, J=1.5 Hz, 8.0 Hz, 1H) 7.49 (m, 2H), 7.38 (dt, J=1.5 Hz, 8.0 Hz, 1H), 4.96 (s, 2H), 3.94 (s, 3H). MS (APCI+): 231 (100), 229 (93).

Intermediate 2:
6-Bromomethyl-pyridine-2-carboxylic acid methyl ester

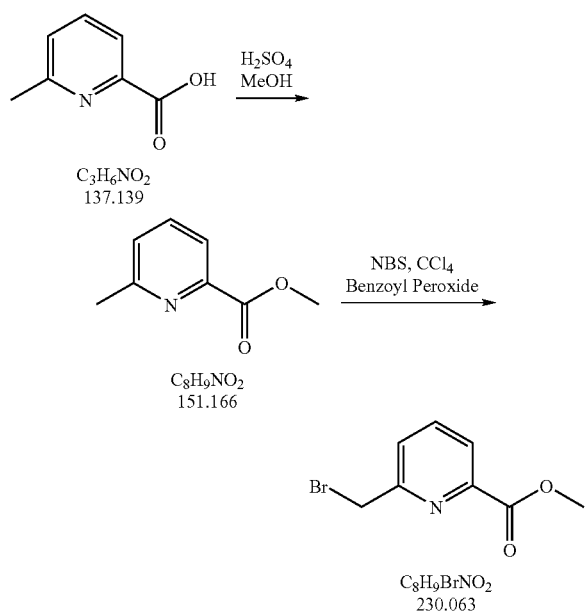

Step 1: 6-Methyl-pyridine-2-carboxylic acid methyl ester

A mixture of 6-methyl-pyridine-2-carboxylic acid (10 g, 72.9 mmol) and concentrated sulfuric acid (3.5 mL) in methanol (300 mL) was heated at reflux overnight. The reaction mixture was cooled to room temperature and concentrated under reduced pressure. The residue was poured into saturated aqueous sodium hydrogen carbonate (250 mL), and extracted with ethyl acetate (3×100 mL). The combined organic layers were dried (magnesium sulfate), filtered, and evaporated to give 6-methyl-pyridine-2-carboxylic acid methyl ester (6.5 g, 59%) as a colorless oil. ¹HNMR (CDCl₃): δ 7.97 (d, J=7.6 Hz, 1H), 7.73 (dd, J=7.6 Hz, 1H), 7.36 (d, J=7.6 Hz, 1H), 4.01 (s, 3H), 2.67 (s, 3H).

Step 2: 6-Bromomethyl-pyridine-2-carboxylic acid methyl ester

6-Bromomethyl-pyridine-2-carboxylic acid methyl ester was prepared according to Wells, G. J. et al. (WO 94/11398): A mixture of 6-methyl-pyridine-2-carboxylic acid methyl ester (6.5 g, 43.0 mmol), benzoyl peroxide (25 mg, 0.1 mmol) and NEBS (8.5 g, 47.8 mmol) in carbon tetrachloride (250 mL) was heated at reflux overnight. The reaction mixture was cooled to room temperature, filtered, evaporated, and purified by chromatography on flash silica gel, eluting with 15% ethyl acetate/hexane to give 6-bromomethyl-pyridine-2-carboxylic acid methyl ester (2.0 g, 20%) as a white solid. ¹HNMR (CDCl₃): δ 8.06 (d, J=8.0 Hz, 1H), 7.87 (dd, J=8.0 Hz, 1H), 7.70 (d, J=8.0 Hz, 1H), 4.65 (s, 2H), 4.02 (s, 3H). MS (APCI+): 231 (45), 235 (42).

Intermediate 3:
2-Bromomethyl-thiazole-4-carboxylic acid ethyl ester

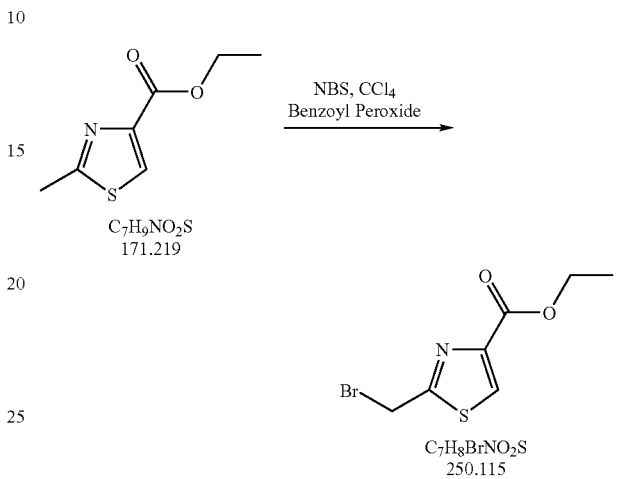

2-Bromomethyl-thiazole-4-carboxylic acid ethyl ester was prepared according to Kindon, N et al. (U.S. Pat. No. 6,162,808): A mixture of 2-methyl-thiazole-4-carboxylic acid (available from Maybridge plc, Tintagel, UK, 9.8 g, 57.2 mmol), benzoyl peroxide (40 mg, 0.165 mmol) and NBS (10.6 g, 60.0 mmol) in carbon tetrachloride (250 mL) was heated at reflux over the weekend. The reaction mixture was cooled to room temperature and evaporated under reduced pressure. The crude material was partitioned between ethyl acetate and water. The organic layer was dried (magnesium sulfate), filtered evaporated, and purified by chromatography on flash silica gel, eluting with 20% ethyl acetate/hexane to give 2-bromomethyl-thiazole-4-carboxylic acid ethyl ester (4.4 g, 31%) as an orange oil. ¹HNMR (CDCl₃): δ 9.23 (s, 1H), 4.77 (s, 2H), 4.44 (q, J=7.0 Hz, 2H), 1.41 (t, J=7.0 Hz, 3H). MS (APCI+): 252 (100), 250 (90).

Intermediate 4:
4-Chloromethyl-thiazole-2-carboxylic acid ethyl ester

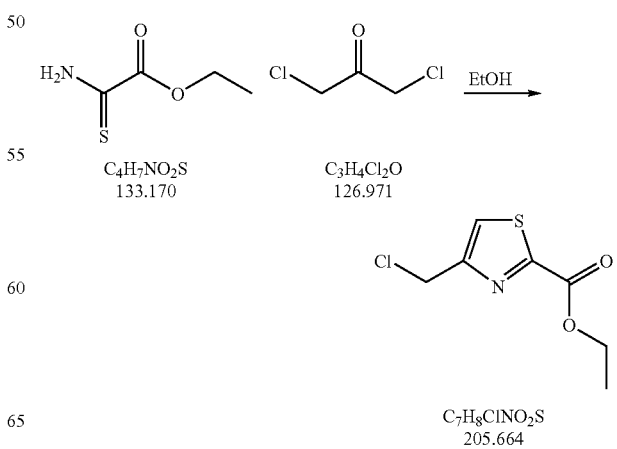

4-Chloromethyl-thiazole-2-carboxylic acid ethyl ester was prepared according to Summers, J. B., Jr. et al. (U.S. Pat. No. 5,486,525): A mixture of ethyl thiooxamate (7.0 g, 52.6 mmol) and 1,3-dichloroacetone (7.0 g, 55.1 mmol) in ethanol (300 mL) was heated at reflux overnight. The solvent was evaporated under reduced pressure, and the crude material was partitioned between methylene chloride and aqueous sodium hydrogen carbonate. The organic layer was dried (magnesium sulfate), filtered, evaporated and purified by chromatography on flash silica gel, eluting with 15% ethyl acetate/hexane to give 4-chloromethyl-thiazole-2-carboxylic acid ethyl ester (4.0 g, 37%) as an orange oil. $^1$HNMR (CDCl$_3$): δ 7.64 (s, 1H), 4.78 (s, 2H), 4.51 (q, J=7.0 Hz, 2H), 1.46 (t, J=7.0 Hz, 3H). MS (APCI+): 206 (100).

Intermediate 5: 4'-Methyl-biphenyl-4-ol

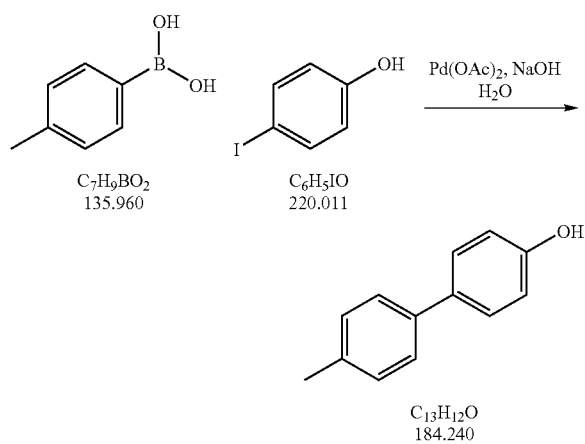

Palladium(II) acetate (52 mg, 0.23 mmol) was added to a mixture of 4-iodophenol (5.00 g, 22.7 mmol), 4-methyl-phenyl-boronic acid (3.4 g, 25.0 mmol), sodium hydroxide (3.6 g, 90 mmol), and water (9 mL). The mixture was diluted twice with water (9 mL) to facilitate stirring. An exotherm occurred, and after 15 minutes the internal temperature was 50° C. The reaction mixture was cooled to room temperature and allowed to stir overnight, and the solid was filtered off, washed with water, and dissolved in ethyl acetate. The organic solution was washed with water three times with 1 M NaOH, and then again with water until the washings were neutral. The solution was then dried (sodium sulfate), filtered, and evaporated to give 4'-methyl-biphenyl-4-ol (2 g, 48%).

Intermediate 6:
5-(4-Iodo-phenoxymethyl)-furan-2-carboxylic acid methyl ester

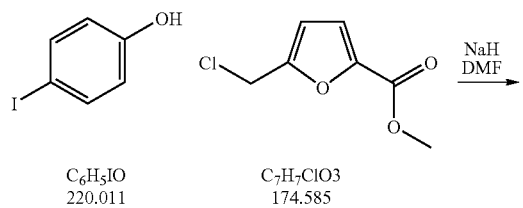

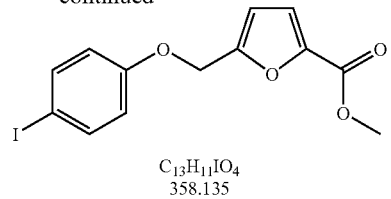

A solution of 4-iodophenol (10.08 g, 45.8 mmol) in N,N-dimethylformamide (30 mL) was added to a ice-bath cooled suspension of sodium hydride (60%; 1.65 g, 41.2 mmol) in N,N-dimethylformamide (30 mL). The ice bath was removed and the mixture was stirred for 1 h. The mixture was cooled again to ~5° C. and a solution of 5-(chloro-methyl)-furan-2-carboxylic acid methyl ester (4.00 g, 22.9 mmol) in N,N-dimethylformamide (60 mL) was added. The reaction mixture was stirred overnight at room temperature, then the solvents were evaporated under reduced pressure and water was added. The mixture was extracted three times with ethyl acetate and the combined organic layers were washed twice with 1 M NaOH, and once each with water and brine. The organic solution was dried (magnesium sulfate) filtered, evaporated, and purified using a Biotage 65 L purification system, eluting with 3% methylene chloride/toluene to give 5-(4-iodo-phenoxymethyl)-furan-2-carboxylic acid methyl ester (2.3 g, 28%) as a white solid, along with some mixed fractions.

Intermediate 7:
5-Bromomethyl-thiophene-2-carboxylic acid methyl ester

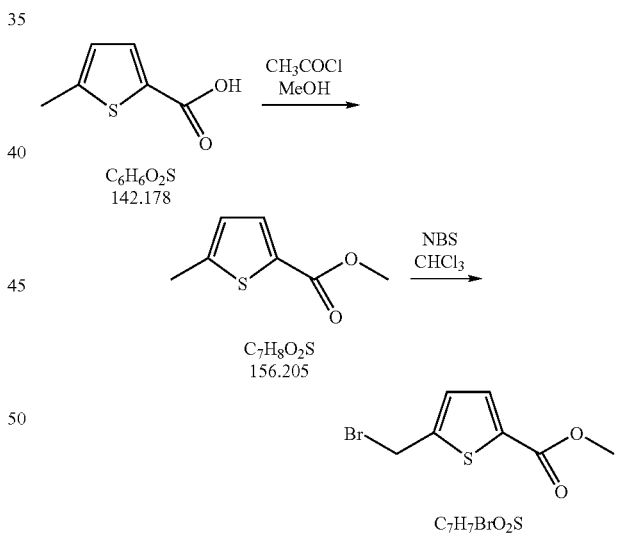

Step 1. 5-Methyl-thiophene-2-carboxylic acid methyl ester

Acetyl chloride (5 mL) was added to a 0° C. solution of methanol (40 mL) and the solution was allowed to warm to room temperature. 5-Methyl-thiophene-2-carboxylic acid (Lancaster; 1.58 g, 11.1 mmol) was added and the solution was allowed to stir at room temperature over the weekend. The solvents were evaporated under reduced pressure and ethyl acetate was added. The solution was extracted with aqueous sodium hydrogen carbonate and the aqueous layer was back-extracted with ethyl acetate. The combined organic layers were dried (sodium sulfate) filtered and evaporated to give 5-methyl-thiophene-2-carboxylic acid methyl ester (1.40 g, 81%) as a yellow oil.

Step 2. 5-Bromomethyl-thiophene-2-carboxylic acid methyl ester

N-Bromosuccinimide (Aldrich; 1.70 g, 9.6 mmol) and a catalytic amount of benzoyl peroxide were added to a solution of 5-methyl-thiophene-2-carboxylic acid methyl ester (1.40 g, 9.0 mmol) in chloroform (15 mL). The reaction mixture was stirred under argon at reflux (~60° C.) for 3 h, then filtered through Celite™ and evaporated under reduced pressure to give 5-bromomethyl-thiophene-2-carboxylic acid methyl ester (2 g) as a yellow oil which was used directly in the next step without further purification.

Intermediate 8: 5-(Biphenyl-4-yloxymethyl)-furan-2-carboxylic acid

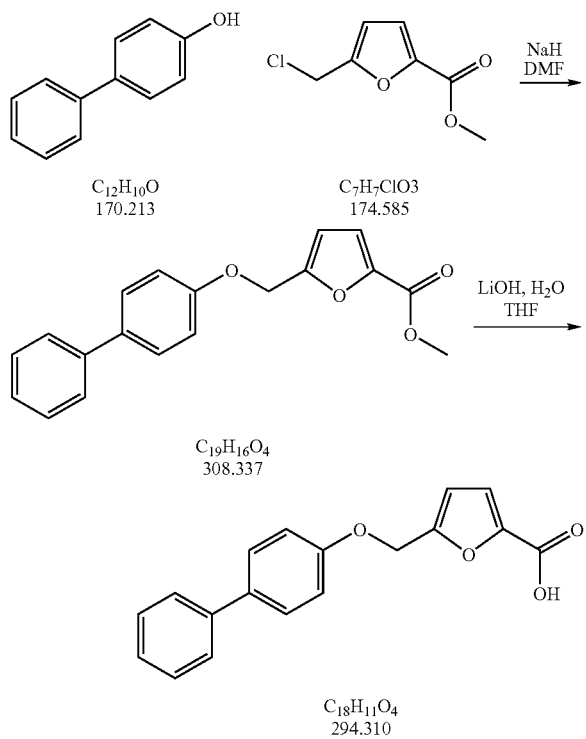

Step 1: 5-(biphenyl-4-yloxymethyl)-furan-2-carboxylic acid methyl ester

N,N-Dimethylformamide (400 mL) was added to sodium hydride (60% dispersion, ~16 g, 0.4 mol) which had been washed with hexanes. The mixture was cooled to ~5° C., and then a solution of 4-phenylphenol (73.12 g, 0.43 mmol) in N,N-dimethylformamide (150 mL) was added. The mixture was allowed to stir at room temperature for 2.5 h, and then a solution of 5-chloromethylfuran-2-carboxylic acid methyl ester (25 g, 0.14 mmol) in N,N-dimethylformamide (100 mL) was added. The reaction mixture was heated at ~105° C. for 2 h, and then it was allowed to cool, evaporated under reduced pressure, and water was added. The mixture was extracted three times with ethyl acetate, and the combined organic layers were washed with saturated brine, dried (magnesium sulfate), filtered, evaporated, and purified using a Biotage 75 L purification system, eluting with 0-10% methylene chloride/toluene to give 5-(biphenyl-4-yloxymethyl)-furan-2-carboxylic acid methyl ester (20.5 g, 46%).

Step 2: 5-(Biphenyl-4-yloxymethyl)-furan-2-carboxylic acid

A solution of lithium hydroxide monohydrate (5.10 g, 121.5 mmol) in water (50 mL) was added to a solution of 5-(biphenyl-4-yloxymethyl)-furan-2-carboxylic acid methyl ester (15.00 g, 48.6 mmol) in tetrahydrofuran (450 mL). The reaction mixture was stirred at room temperature for 72 h. The solvents were evaporated and water was added. The mixture was extracted three times with ether. Insoluble white solid was filtered off. The pH of the aqueous solution was adjusted to 3 and the resulting mixture was extracted with ethyl acetate (3×500 mL). The combined organic layers were washed with 50% saturated brine and then evaporated under reduced pressure to give 5-(biphenyl-4-yloxymethyl)-furan-2-carboxylic acid (12.0 g, 84%) as a white solid.

General Procedure A for the Preparation of Biaryloxymethylarene-Carboxylic Acids Potassium carbonate (150 mg, 1.09 mmol) was added to a solution of the phenol (0.30 mmol) in DMF (0.7 mL) and the mixture was agitated for 15 min. Potassium iodide (4.5 mg, 0.093 mmol) and a solution of the chloro- or bromomethylarenecarboxylic acid ester (0.41 mmol) in DMF (0.7 mL) were added. The resultant mixture was agitated at 80° C. for 2 days. The reaction mixture was cooled to room temperature, and partitioned between ethyl acetate (15 mL) and aqueous potassium hydroxide (1 M, 15 mL). The organic layer was passed through a pad of magnesium sulfate and dried in vacuo to give the lower alkyl ester.

The lower alkyl ester was dissolved in tetrahydrofuran:methanol:water (3:1:1). Lithium hydroxide monohydrate (4 equiv.) was added. The resultant mixture was agitated at 75° C. for 2 days and then evaporated under reduced pressure, and the residue was partitioned between ethyl ether (15 mL) and aqueous potassium hydroxide (0.5 M, 15 mL). The aqueous layer was separated, acidified to pH 1 by addition of 1 M HCl, and extracted twice with ethyl acetate. The organic layer was passed through a pad of magnesium sulfate and dried in vacuo.

General Procedure B for the Preparation of Biaryloxymethylarene-Carboxylic Acids Potassium carbonate (150 mg, 1.09 mmol) was added to a solution of the phenol (0.30 mmol) in DMF (0.7 mL) and the mixture was agitated for 15 min. Potassium iodide (4.5 mg, 0.093 mmol) and a solution of the chloro- or bromomethylarenecarboxylic acid ester (0.41 mmol) in DMF (0.7 mL) were added. The resultant mixture was agitated at 80° C. for 2 days. The reaction mixture was cooled to room temperature, and partitioned between ethyl acetate (15 mL) and aqueous potassium hydroxide (1 M, 15 mL). The organic layer was passed through a pad of magnesium sulfate and dried in vacuo to give the lower alkyl ester.

The lower alkyl ester was dissolved in tetrahydrofuran:methanol:water (3:1:1). Lithium hydroxide monohydrate (4 equiv.) was added. The resultant mixture was agitated at 75° C. for 2 days and then partitioned between ethyl ether (15 mL) and aqueous potassium hydroxide (0.5 M, 15 mL). The aqueous layer was separated, acidified to pH 1 by addition of 1 M HCl, and extracted twice with ethyl acetate. The organic layer was passed through a pad of magnesium sulfate and dried in vacuo.

Example 1

3-(3-Chloro-biphenyl-4-yloxymethyl)-benzoic acid

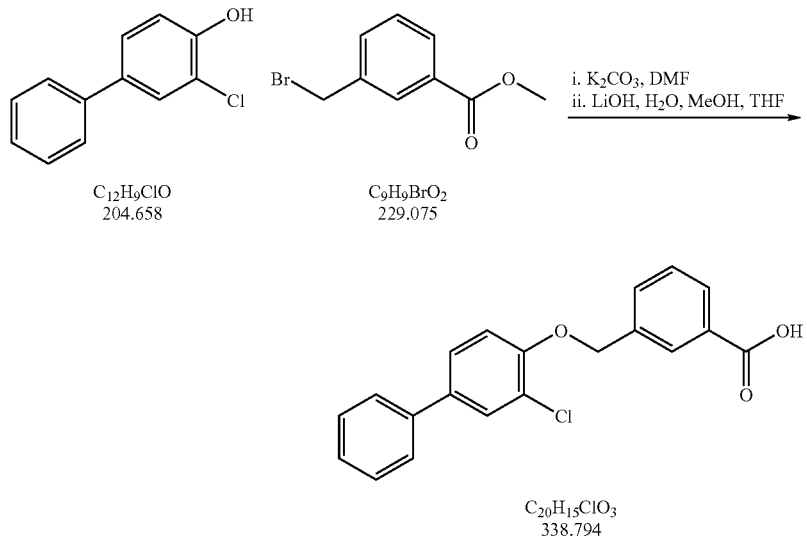

3-(3-Chloro-biphenyl-4-yloxymethyl)-benzoic acid was prepared using general procedure A from 2-chloro-4-phenylphenol (available from TCI America, Portland, Oreg.) and 3-(bromomethyl)benzoic acid methyl ester (available from Lancaster Synthesis Ltd., Morcambe, Lancashire, UK). Yield: 76 mg. Mass spectrum MH+=339.

Example 2

3-(Biphenyl-3-yloxymethyl)-benzoic acid

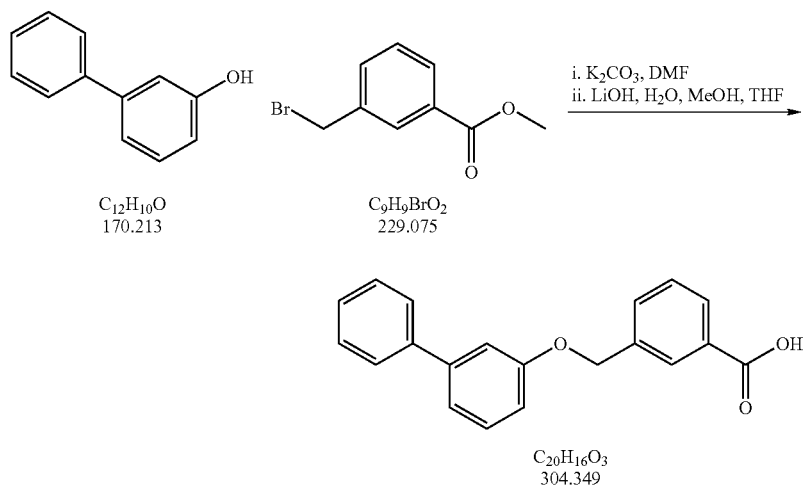

3-(Biphenyl-3-yloxymethyl)-benzoic acid was prepared using general procedure A from 3-phenylphenol (available from Aldrich, Milwaukee, Wis.) and 3-(bromomethyl)benzoic acid methyl ester (available from Lancaster Synthesis Ltd., Morcambe, Lancashire, UK). Yield: 76 mg. Mass spectrum (ES) MH+=305.

Example 3

3-(4'-Methyl-biphenyl-4-yloxymethyl)-benzoic acid

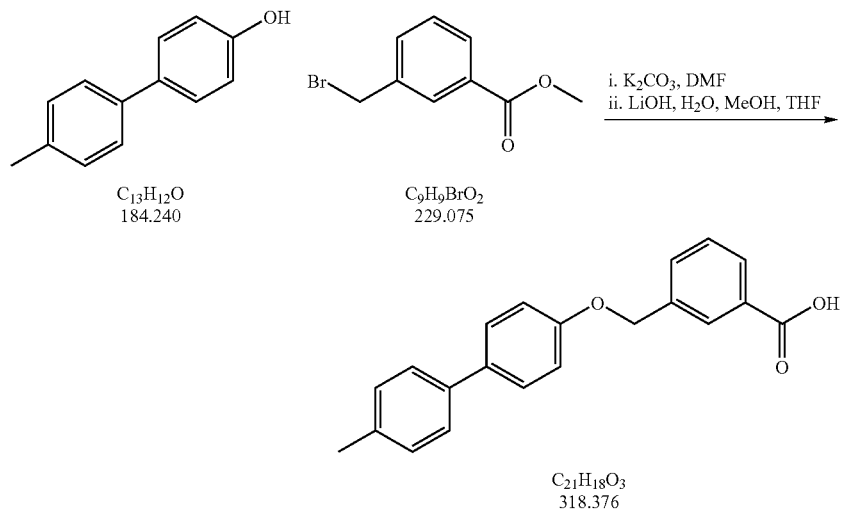

3-(4'-Methyl-biphenyl-4-yloxymethyl)-benzoic acid was prepared using general procedure A from 4'-methyl-biphenyl-4-ol (purchased from Maybridge plc, Tintagel, Cornwall, UK or from Intermediate 5) and 3-(bromomethyl)benzoic acid methyl ester (available from Lancaster Synthesis Ltd., Morcambe, Lancashire, UK). Yield: 66 mg. Mass spectrum (ES) MH+=319.

Example 4

3-(4'-Bromo-biphenyl-4-yloxymethyl)-benzoic acid

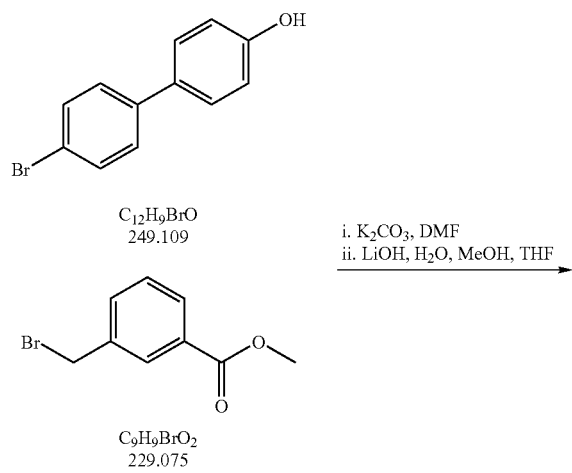

3-(4'-Bromo-biphenyl-4-yloxymethyl)-benzoic acid was prepared using general procedure A from 4-bromo-4'-hydroxybiphenyl (available from TCI America, Portland, Oreg.) and 3-(bromomethyl)benzoic acid methyl ester (available from Lancaster Synthesis Ltd., Morcambe, Lancashire, UK). Yield: 91 mg. Mass spectrum (ES) MH+=383.

Example 5

3-(4'-Chloro-biphenyl-4-yloxymethyl)-benzoic acid

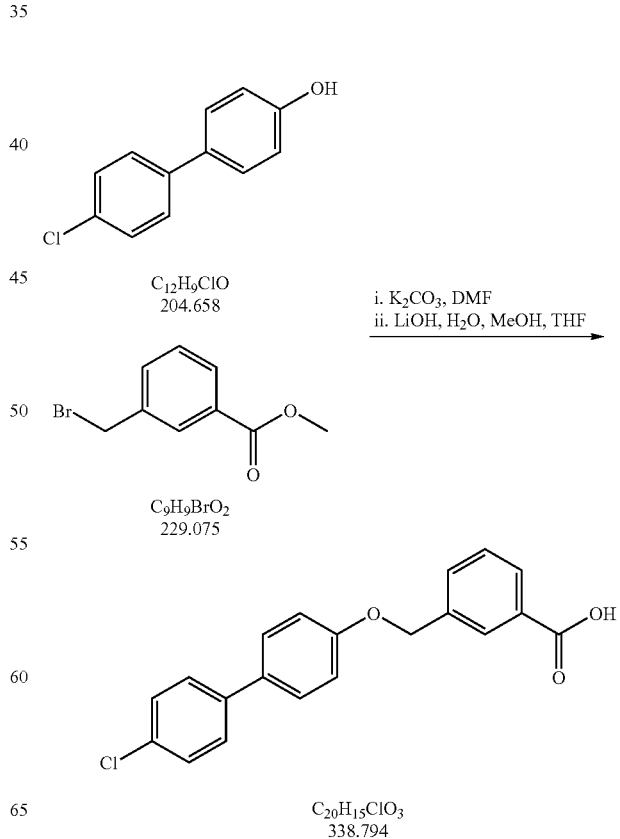

3-(4'-Chloro-biphenyl-4-yloxymethyl)-benzoic acid was prepared using general procedure A from 4-chloro-4'-hydroxybiphenyl (available from TCI America, Portland, Oreg.) and 3-(bromomethyl)benzoic acid methyl ester (available from Lancaster Synthesis Ltd., Morcambe, Lancashire, UK). Yield: 80 mg. Mass spectrum (ES) MH+=339.

Example 6

3-(2'-Nitro-biphenyl-4-yloxymethyl)-benzoic acid

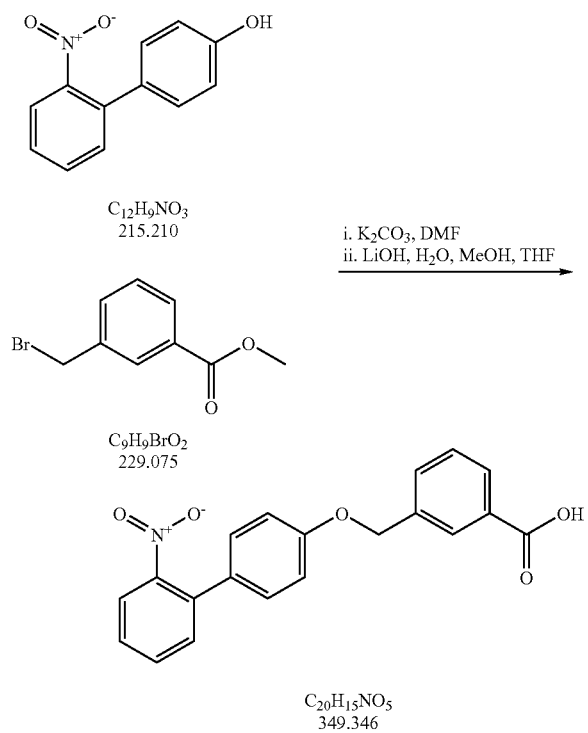

3-(2'-Nitro-biphenyl-4-yloxymethyl)-benzoic acid was prepared using general procedure A from 4-hydroxy-2'-nitrobiphenyl (available from TCI America, Portland, Oreg.) and 3-(bromomethyl)benzoic acid methyl ester (available from Lancaster Synthesis Ltd. Morcambe, Lancashire, UK). Yield: 82 mg. Mass spectrum (ES) MH+=350.

Example 7

3-(4'-Methoxy-biphenyl-4-yloxymethyl)-benzoic acid

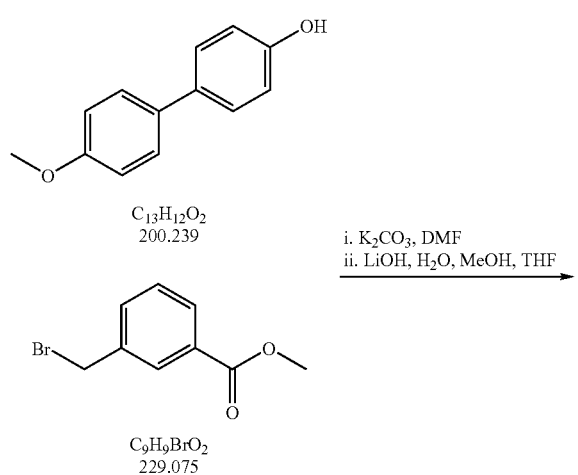

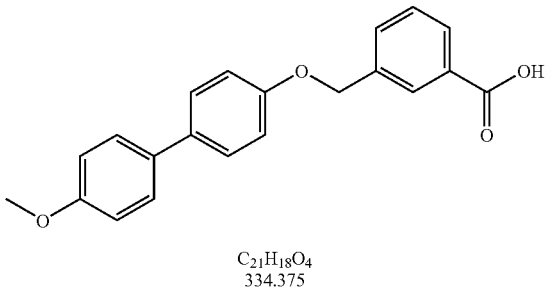

3-(4'-Methoxy-biphenyl-4-yloxymethyl)-benzoic acid was prepared using general procedure A from 4-hydroxy-4'-methoxybiphenyl (available from TCI America, Portland, Oreg.) and 3-(bromomethyl)benzoic acid methyl ester (available from Lancaster Synthesis Ltd. Morcambe, Lancashire, UK). Yield: 73 mg. Mass spectrum (ES) MH+=335.

Example 8

5-(3-Chloro-biphenyl-4-yloxymethyl)-furan-2-carboxylic acid

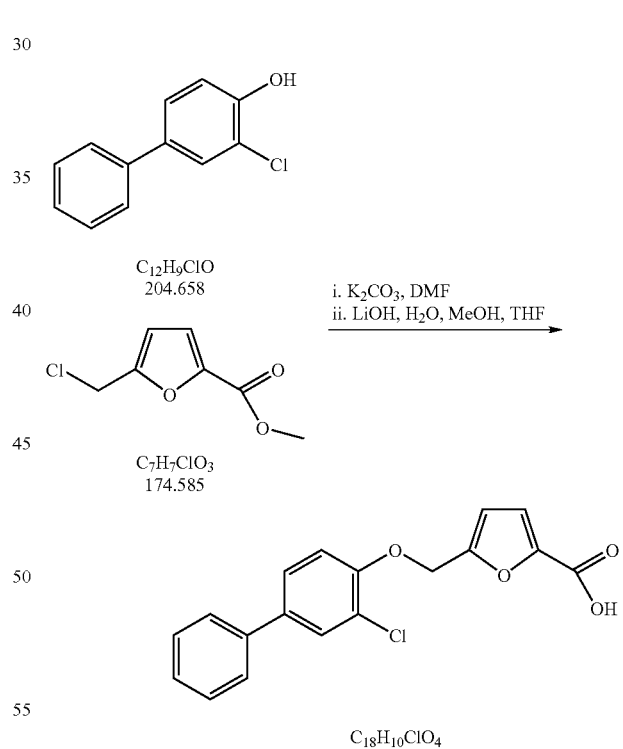

5-(3-Chloro-biphenyl-4-yloxymethyl)-furan-2-carboxylic acid was prepared using general procedure A from 2-chloro-4-phenylphenol (available from TCI America, Portland, Oreg.) and 5-chloromethylfuran-2-carboxylic acid methyl ester (available from Aldrich, Milwaukee, Wis., or from Maybridge plc, Tintagel, UK). Yield: 66 mg. Mass spectrum (ES) MH+=329.

Example 9

5-(Biphenyl-3-yloxymethyl)-furan-2-carboxylic acid

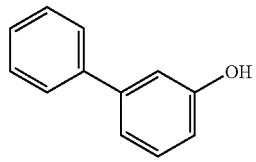

C₁₂H₁₀O
170.213

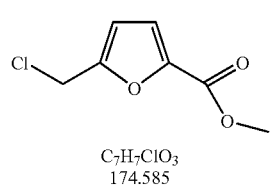

C₇H₇ClO₃
174.585 i. K₂CO₃, DMF
ii. LiOH, H₂O, MeOH, THF
→

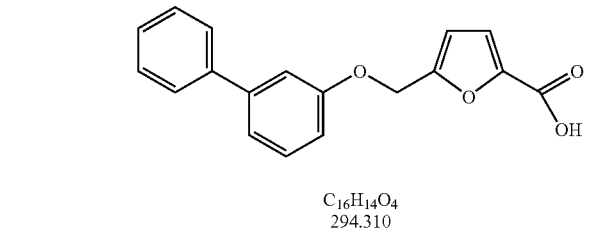

C₁₆H₁₄O₄
294.310

5-(Biphenyl-3-yloxymethyl)-furan-2-carboxylic acid was prepared using general procedure A from 3-phenylphenol (available from Aldrich, Milwaukee, Wis.) and 5-chloromethylfuran-2-carboxylic acid methyl ester (available from Aldrich, Milwaukee, Wis., or from Maybridge plc, Tintagel, UK), Yield: 67 mg. Mass spectrum (ES) MH+=295.

Example 10

5-(4'-Methyl-biphenyl-4-yloxymethyl)-furan-2-carboxylic acid

Method 1. From 4'-methyl-biphenyl-4-ol and 5-chloromethylfuran-2-carboxylic acid methyl ester

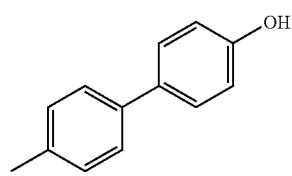

C₁₃H₁₂O
184.230

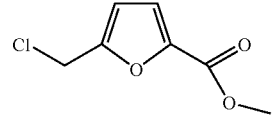

C₇H₇ClO₃
174.585 i. K₂CO₃, DMF
ii. LiOH, H₂O, MeOH, THF
→

-continued

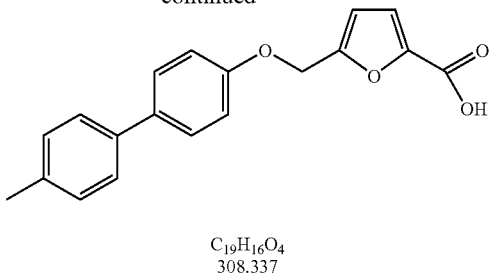

C₁₉H₁₆O₄
308.337

5-(4'-Methyl-biphenyl-4-yloxymethyl)-furan-2-carboxylic acid was prepared using general procedure A from 4'-methyl-biphenyl-4-ol (purchased from Maybridge plc, Tintagel, Cornwall, UK or from Intermediate 5) and 5-chloromethyl-furan-2-carboxylic acid methyl ester (available from Aldrich, Milwaukee, Wis., or from Maybridge plc, Tintagel, UK). Yield: 47 mg. Mass spectrum (ES) MH+=309.

Method 2.

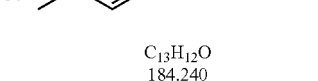

C₁₃H₁₂O
184.240

NaH
DMF
→

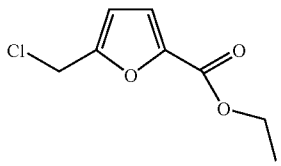

C₈H₉ClO3
188.612

C₂₁H₂₀O₄
336.391

LiOH, H₂O
THF, MeOH
→

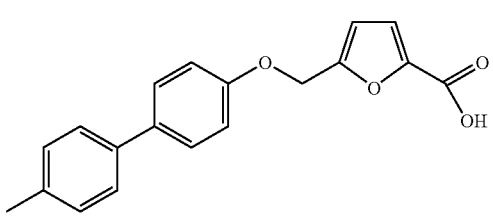

C₁₉H₁₆O₄
308.337

Step 1: 5-(4-Methyl-biphenyl-4-yloxymethyl)-furan-2-carboxylic acid ethyl ester 4'-Methyl-biphenyl-4-ol (Intermediate 5; 2.0 g, 10.9 mmol) was added to a suspension of sodium hydride (60% dispersion; 384 mg, 9.6 mmol) in N,N-dimethylformamide (30 mL) and the mixture was stirred at −5° C. for 20 min. A solution of 5-(chloro-methyl)-furan-2-carboxylic acid ethyl ester (1.6 g, 8.5 mmol) in N,N-dimethylformamide (60 mL) was added and the reaction mixture was stirred overnight at room temperature. The solvents were evaporated under reduced pressure and the residue was partitioned between water and ethyl acetate. The aqueous layer was extracted twice with ethyl acetate, and the combined organic layers were washed with water and brine, dried (sodium sulfate) filtered, evaporated and chromatographed, eluting with 0-50% methylene chloride/hexanes to give 5-(4'-methyl-biphenyl-4-yloxymethyl)-furan-2-carboxylic acid ethyl ester (2.4 g, 84%).

Step 2: 5-(4'-Methyl-biphenyl-4-yloxymethyl)-furan-2-carboxylic acid

A solution of 5-(4'-methyl-biphenyl-4-yloxymethyl)-furan-2-carboxylic acid ethyl ester (2.00 g, 5.9 mmol) in tetrahydrofuran (30 mL) and methanol (10 mL) was added to a solution of lithium hydroxide monohydrate (0.476 g, 11.3 mmol) in water (15 mL). Methanol (5 mL) and tetrahydrofuran (10 mL) were added, and the reaction mixture was stirred at room temperature overnight. The solvents were evaporated, and the residue was suspended in water and acidified to pH 2.5 with 1 M HCl. The resulting white solid was filtered off, and twice suspended in ethyl acetate and evaporated to give 5-(4'-methyl-biphenyl-4-yloxymethyl)-furan-2-carboxylic acid (1.6 g, 88%) as a white solid.

Method 3. From 5-(4-iodo-phenoxymethyl)-furan-2-carboxylic acid methyl ester and 4-methyl-phenyl-boronic acid

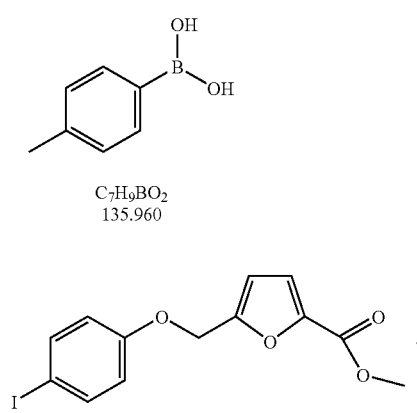

A mixture of 5-(4-iodo-phenoxymethyl)-furan-2-carboxylic acid methyl ester (Intermediate 6; 100 mg, 0.28 mmol), 4-methyl-phenyl-boronic acid (42 mg, 0.31 mmol), sodium hydroxide (45 mg, 1.13 mmol), palladium(II) acetate (2 mg, 0.01 mmol) and water (10 mL) was heated at ~50° C. overnight. The mixture was filtered and the residue was washed with water, ethyl acetate, methylene chloride, and methanol. The aqueous layer was acidified and extracted three times with ethyl acetate. The combined organic layers were washed with water and saturated brine, dried (magnesium sulfate), filtered, and evaporated to give 5-(4'-methyl-biphenyl-4-yloxymethyl)-furan-2-carboxylic acid (80 mg, 84%) as a white solid.

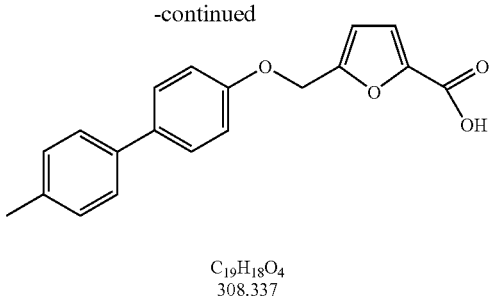

$C_{19}H_{18}O_4$
308.337

Example 11

5-(4'-Bromo-biphenyl-4-yloxymethyl)-furan-2-carboxylic acid

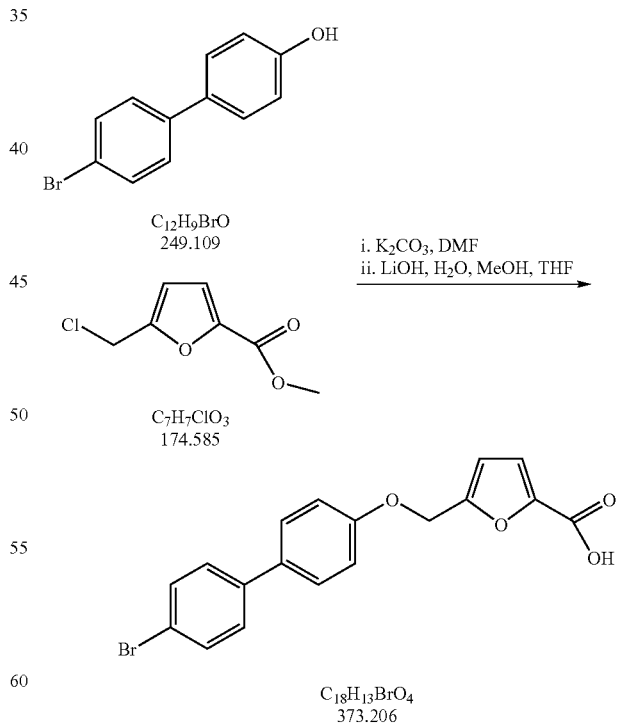

5-(4'-Bromo-biphenyl-4-yloxymethyl)-furan-2-carboxylic acid was prepared using general procedure A from 4-bromo-4'-hydroxybiphenyl (available from TCI America, Portland, Oreg.) and 5-chloromethylfuran-2-carboxylic acid methyl ester (available from Aldrich, Milwaukee, Wis., or from Maybridge plc, Tintagel, UK). Yield: 86 mg. Mass spectrum (ES) MH+=373.

Example 12

5-(4'-Chloro-biphenyl-4-yloxymethyl)-furan-2-carboxylic acid

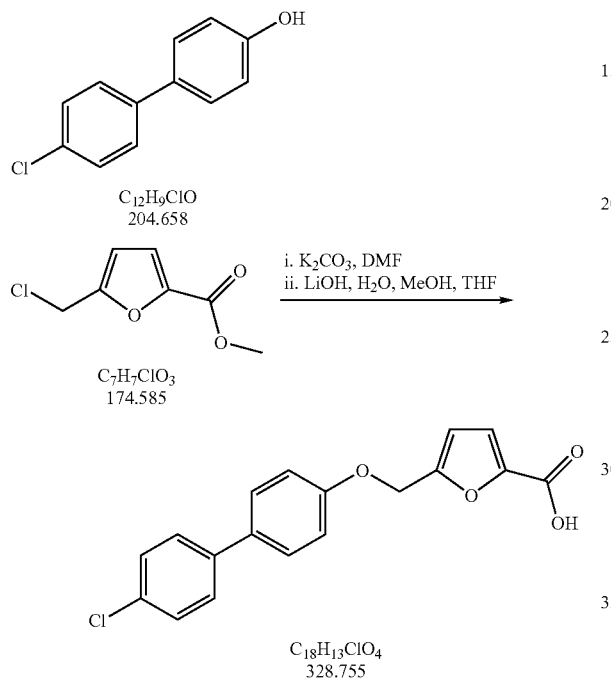

5-(4'-Chloro-biphenyl-4-yloxymethyl)-furan-2-carboxylic acid was prepared using general procedure A from 4-chloro-4'-hydroxybiphenyl (available from TCI America, Portland, Oreg.) and 5-chloromethylfuran-2-carboxylic acid methyl ester (available from Aldrich, Milwaukee, Wis., or from Maybridge plc, Tintagel, UK). Yield: 72 mg. Mass spectrum (ES) MH+=329.

Example 13

5-(2'-Nitro-biphenyl-4-yloxymethyl)-furan-2-carboxylic acid

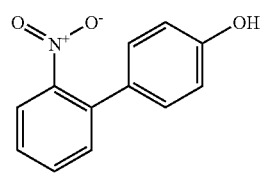

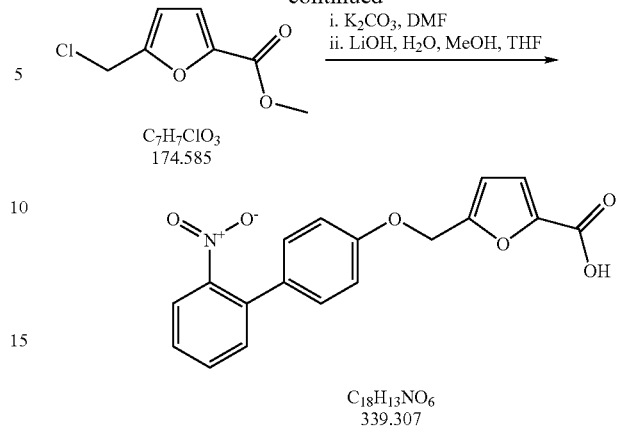

5-(2'-Nitro-biphenyl-4-yloxymethyl)-furan-2-carboxylic acid was prepared using general procedure A from 4-hydroxy-2'-nitrobiphenyl (available from TCI America, Portland, Oreg.) and 5-chloromethylfuran-2-carboxylic acid methyl ester (available from Aldrich, Milwaukee, Wis., or from Maybridge plc, Tintagel, UK). Yield: 82 mg. Mass spectrum (ES) MH+=340.

Example 14

5-(4'-Nitro-biphenyl-4-yloxymethyl)-furan-2-carboxylic acid

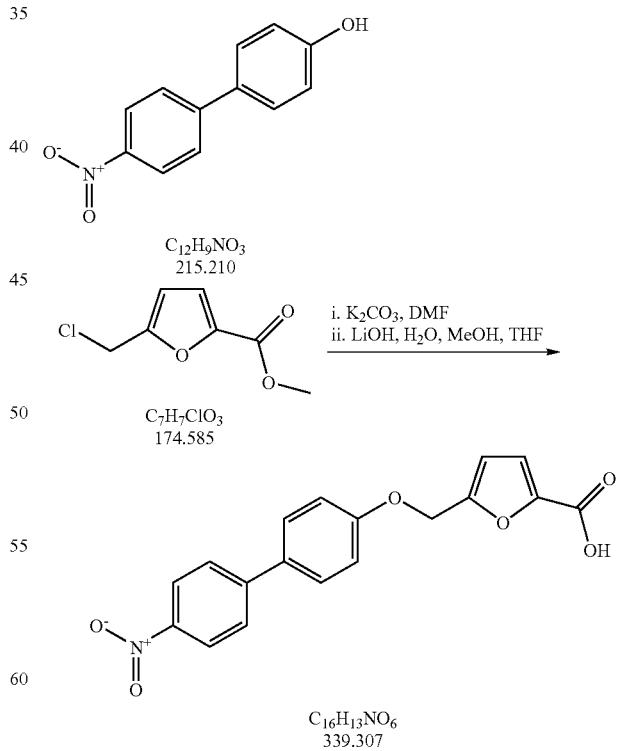

5-(4'-Nitro-biphenyl-4-yloxymethyl)-furan-2-carboxylic acid was prepared using general procedure A from 4-hydroxy-4'-nitrobiphenyl (available from TCI America, Portland, Oreg.) and 5-chloromethylfuran-2-carboxylic acid methyl ester (available from Aldrich, Milwaukee, Wis., or from Maybridge plc, Tintagel, UK). Yield: 40 mg. Mass spectrum (ES) MH+=340.

Example 15

2-(3-Chloro-biphenyl-4-yloxymethyl)-benzoic acid

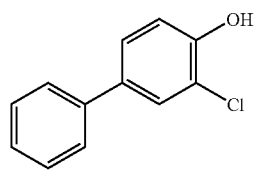

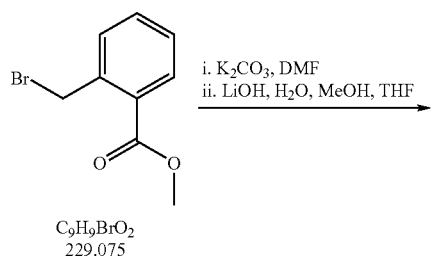

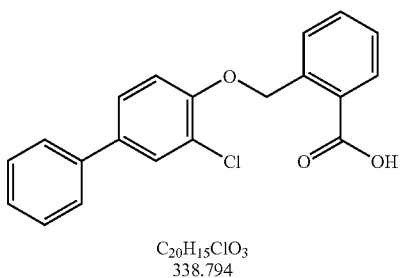

2-(3-Chloro-biphenyl-4-yloxymethyl)-benzoic acid was prepared using general procedure A from 2-chloro-4-phenylphenol (available from TCI America, Portland, Oreg.) and 2-bromomethyl-benzoic acid methyl ester (Intermediate 1). Yield: 45 mg. Mass spectrum (ES) MH+=339.

Example 16

2-(4'-Methyl-biphenyl-4-yloxymethyl)-benzoic acid

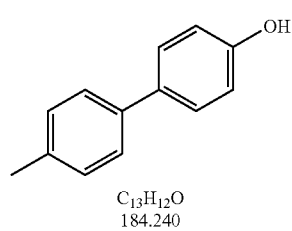

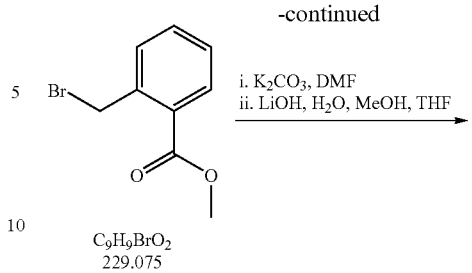

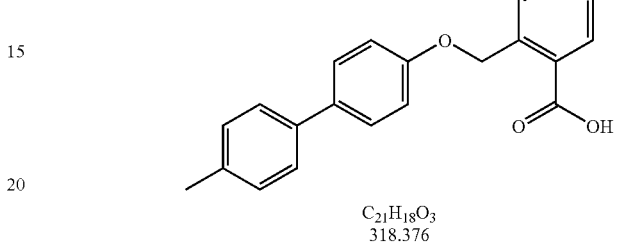

2-(4'-Methyl-biphenyl-4-yloxymethyl)-benzoic acid was prepared using general procedure A from 4'-methyl-biphenyl-4-ol (purchased from Maybridge plc, Tintagel, Cornwall, UK or from Intermediate 5) and 2-bromomethyl-benzoic acid methyl ester (Intermediate 1). Yield: 54 mg. Mass spectrum (ES) MH+=319.

Example 17

2-(2'-Nitro-biphenyl-4-yloxymethyl)-benzoic acid

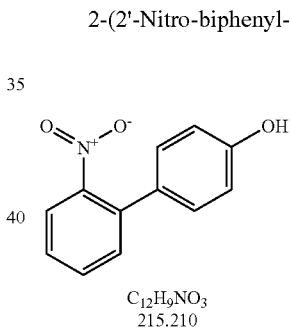

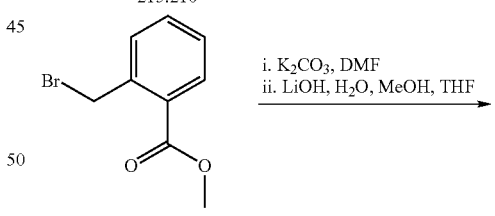

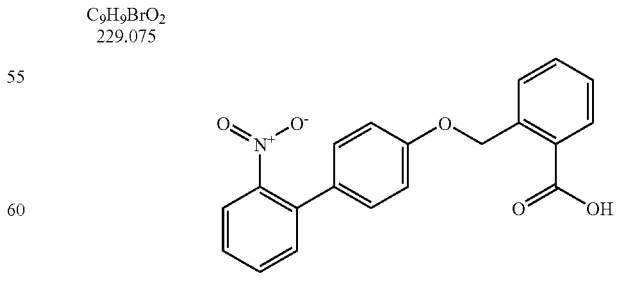

2-(2'-Nitro-biphenyl-4-yloxymethyl)-benzoic acid was prepared using general procedure A from 4'-hydroxy-2-nitrobiphenyl (available from TCI America Portland, Oreg.) and 2-bromomethyl-benzoic acid methyl ester (intermediate 1). Yield: 69 mg. Mass spectrum (ES) MH+=350.

Example 18

2-(Biphenyl-4-yloxymethyl)-benzoic acid

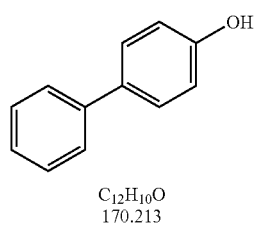

C₁₂H₁₀O
170.213

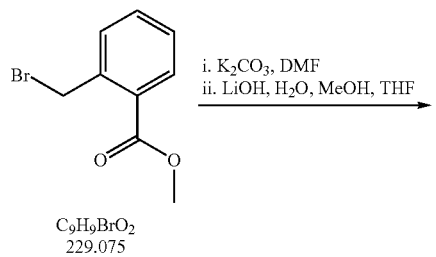

C₉H₉BrO₂
229.075 i. K₂CO₃, DMF
ii. LiOH, H₂O, MeOH, THF

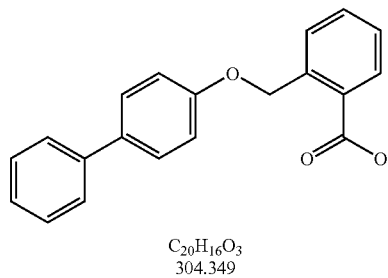

C₂₀H₁₆O₃
304.349

2-(Biphenyl-4-yloxymethyl)-benzoic acid was prepared using general procedure A from 4-phenylphenol (available from Aldrich, Milwaukee, Wis.) and 2-bromomethyl-benzoic acid methyl ester (Intermediate 1). Yield: 50 mg. Mass spectrum (ES) MH+=305.

Example 19

5-(2'-Nitro-biphenyl-4-yloxymethyl)-thiophene-2-carboxylic acid

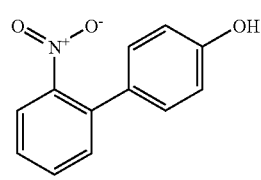

C₁₂H₉NO₃
215.210

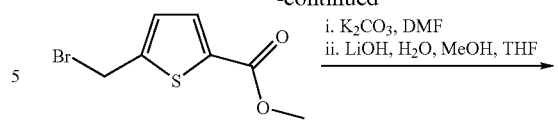

C₇H₇BrO₂S
235.101 i. K₂CO₃, DMF
ii. LiOH, H₂O, MeOH, THF

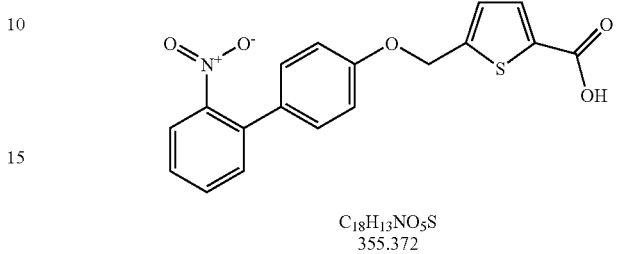

C₁₈H₁₃NO₅S
355.372

5-(2'-Nitro-biphenyl-4-yloxymethyl)-thiophene-2-carboxylic acid was prepared using general procedure A from 4-hydroxy-2'-nitrobiphenyl (available from TCI America, Portland, Oreg.) and 5-bromomethyl-thiophene-2-carboxylic acid methyl ester (Intermediate 7). Yield: 80 mg. Mass spectrum (ES) MH+=356.

Example 20

6-(2'-Nitro-biphenyl-4-yloxymethyl)-pyridine-2-carboxylic acid

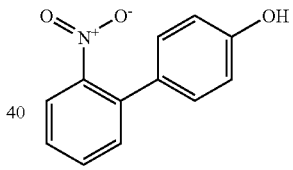

C₁₂H₉NO₅
215.210

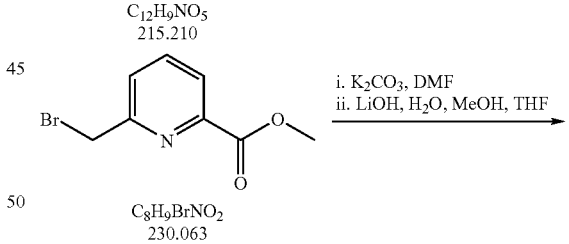

C₈H₉BrNO₂
230.063 i. K₂CO₃, DMF
ii. LiOH, H₂O, MeOH, THF

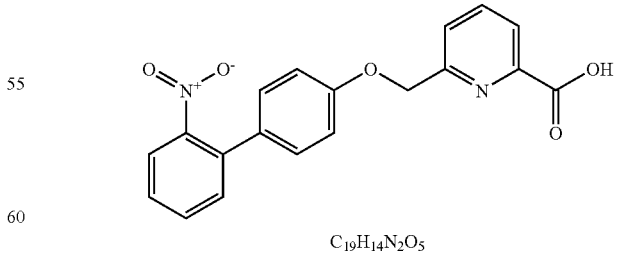

C₁₉H₁₄N₂O₅
350.334

6-(2'-Nitro-biphenyl-4-yloxymethyl)-pyridine-2-carboxylic acid was prepared using general procedure B from 4-hydroxy-2'-nitrobiphenyl (available from TCI America, Portland, Oreg.) and 6-bromomethyl-pyridine-2-carboxylic acid methyl ester (Intermediate 2). Yield: 62 mg. Mass spectrum (ES) MH+=351.

Example 21

6-(Biphenyl-4-yloxymethyl)-pyridine-2-carboxylic acid

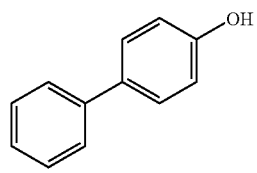

C₁₂H₁₀O
170.213

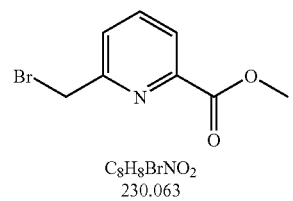

C₈H₈BrNO₂
230.063 i. K₂CO₃, DMF
ii. LiOH, H₂O, MeOH, THF

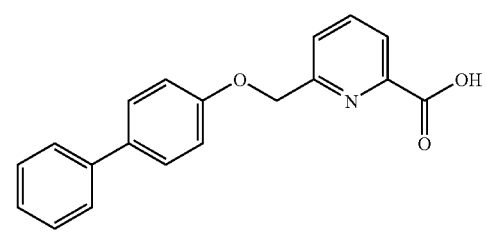

C₁₈H₁₅NO₃
305.336

6-(Biphenyl-4-yloxymethyl)-pyridine-2-carboxylic acid was prepared using general procedure B from 4-phenylphenol (available from Aldrich, Milwaukee, Wis.) and 6-bromomethyl-pyridine-2-carboxylic acid methyl ester (intermediate 2). Yield: 68 mg. Mass spectrum (ES) MH+=306.

Example 22

2-(3-Chloro-biphenyl-4-yloxymethyl)-thiazole-4-carboxylic acid

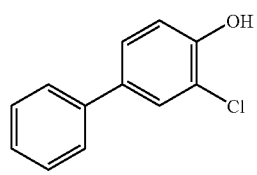

C₁₂H₉ClO
204.658

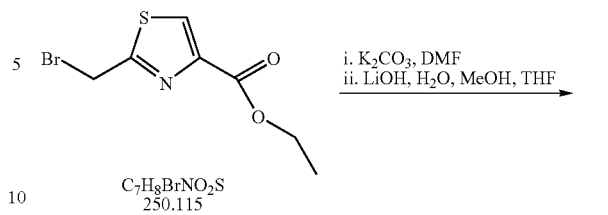

C₇H₈BrNO₂S
250.115 i. K₂CO₃, DMF
ii. LiOH, H₂O, MeOH, THF

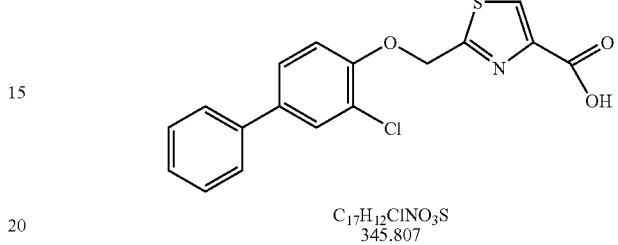

C₁₇H₁₂ClNO₃S
345.807

2-(3-Chloro-biphenyl-4-yloxymethyl)-thiazole-4-carboxylic acid was prepared using general procedure B from 2-chloro-4-phenylphenol (available from TCI America, Portland, Oreg.) and 2-bromomethyl-thiazole-4-carboxylic acid ethyl ester (Intermediate 3). Yield: 82 mg. Mass spectrum (ES) MH+=346.

Example 23

2-(Biphenyl-3-yloxymethyl)-thiazole-4-carboxylic acid

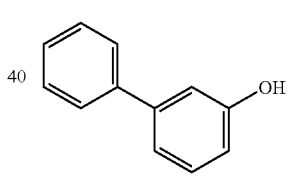

C₁₂H₁₀O
170.213

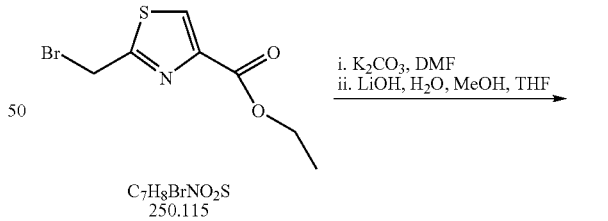

C₇H₈BrNO₂S
250.115 i. K₂CO₃, DMF
ii. LiOH, H₂O, MeOH, THF

C₁₇H₁₃NO₃S
311.362

2-(Biphenyl-3-yloxymethyl)-thiazole-4-carboxylic acid was prepared using general procedure B from 3-phenylphenol (available from Aldrich, Milwaukee, Wis.) and 2-bromomethyl-thiazole-4-carboxylic acid ethyl ester (Intermediate 3). Yield: 65 mg. Mass spectrum (ES) MH+=312.

Example 24

2-(4'-Methyl-biphenyl-4-yloxymethyl)-thiazole-4-carboxylic acid

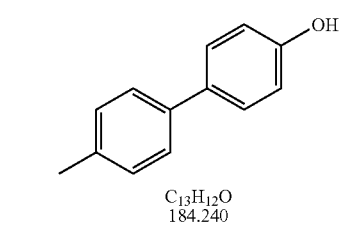

C₁₃H₁₂O
184.240

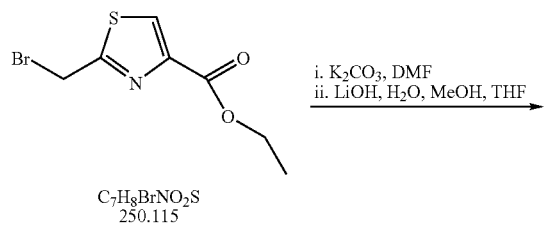

C₇H₈BrNO₂S
250.115 i. K₂CO₃, DMF
ii. LiOH, H₂O, MeOH, THF

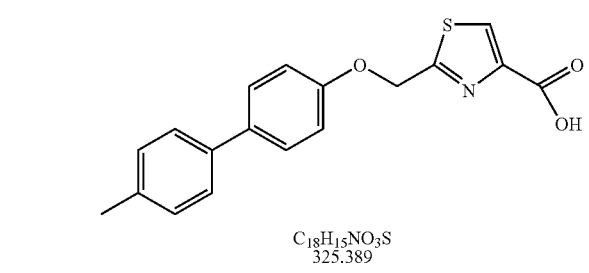

C₁₈H₁₅NO₃S
325.389

2-(4'-Methyl-biphenyl-4-yloxymethyl)-thiazole-4-carboxylic acid was prepared using general procedure B from 4'-methyl-biphenyl-4-ol (purchased from Maybridge plc, Tintagel, Cornwall, UK or from Intermediate 5) and 2-bromomethyl-thiazole-4-carboxylic acid ethyl ester (intermediate 3). Yield: 70 mg. Mass spectrum (ES) MH+=326.

Example 25

2-(4-Bromo-biphenyl-4-yloxymethyl)-thiazole-4-carboxylic acid

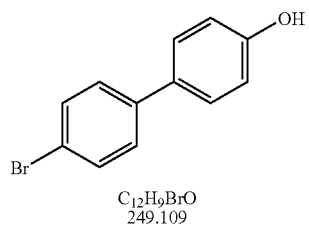

C₁₂H₉BrO
249.109

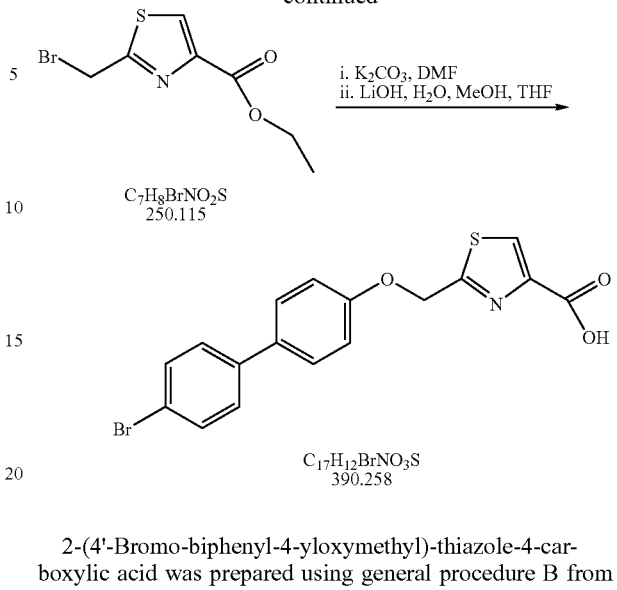

C₇H₈BrNO₂S
250.115 i. K₂CO₃, DMF
ii. LiOH, H₂O, MeOH, THF

C₁₇H₁₂BrNO₃S
390.258

2-(4'-Bromo-biphenyl-4-yloxymethyl)-thiazole-4-carboxylic acid was prepared using general procedure B from 4-bromo-4'-hydroxybiphenyl (available from TCI America, Portland, Oreg.) and 2-bromomethyl-thiazole-4-carboxylic acid ethyl ester (Intermediate 3). Yield: 82 mg. Mass spectrum (ES) MH+=390.

Example 26

2-(4'-Chloro-biphenyl-4-yloxymethyl)-thiazole-4-carboxylic acid

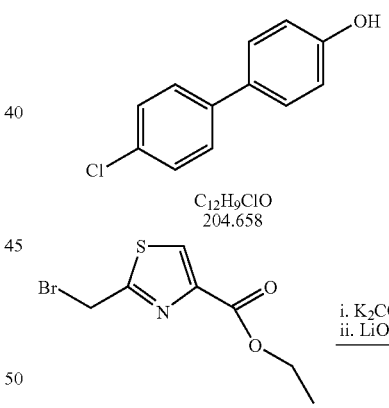

C₁₂H₉ClO
204.658

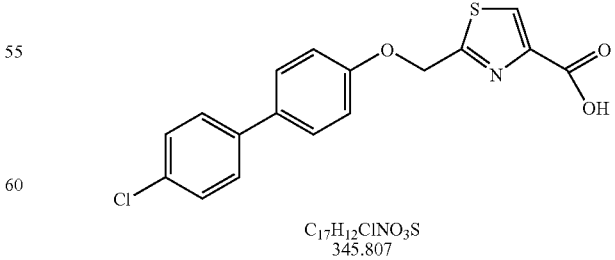

C₇H₈BrNO₂S
250.115 i. K₂CO₃, DMF
ii. LiOH, H₂O, MeOH, THF

C₁₇H₁₂ClNO₃S
345.807

2-(4'-Chloro-biphenyl-4-yloxymethyl)-thiazole-4-carboxylic acid was prepared using general procedure B from 4-chloro-4'-hydroxybiphenyl (available from TCI America, Portland, Oreg.) and 2-bromomethyl-thiazole-4-carboxylic acid ethyl ester (Intermediate 3). Yield: 82 mg. Mass spectrum (ES) MH+=346.

Example 27

2-(2'-Nitro-biphenyl-4-yloxymethyl)-thiazole-4-carboxylic acid

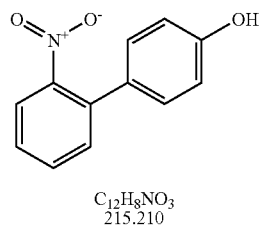

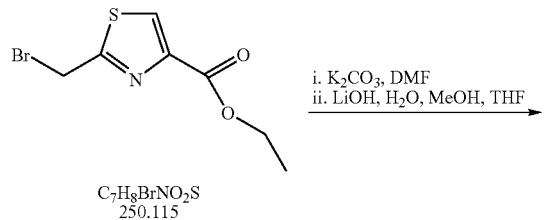

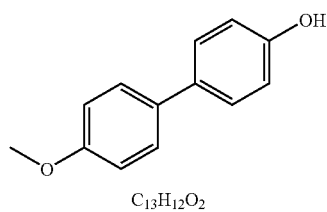

2-(2'-Nitro-biphenyl-4-yloxymethyl)-thiazole-4-carboxylic acid was prepared using general procedure B from 4-hydroxy-4'-methoxybiphenyl (available from TCI America, Portland, Oreg.) and 2-bromomethyl-thiazole-4-carboxylic acid ethyl ester (Intermediate 3). Yield: 82 mg. Mass spectrum (ES) MH+=357.

Example 28

2-(4'-Methoxy-biphenyl-4-yloxymethyl)-thiazole-4-carboxylic acid

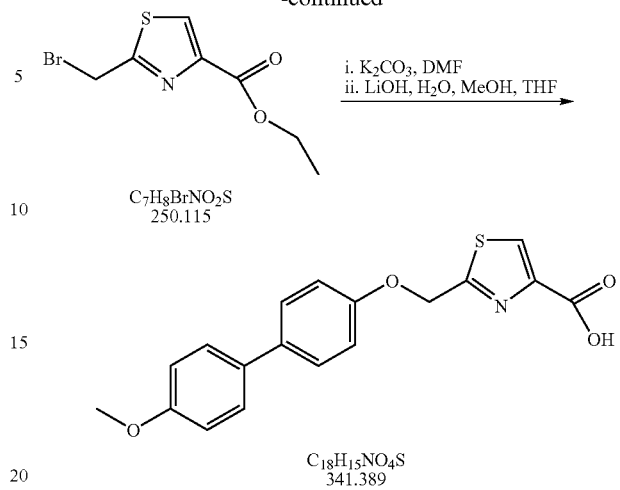

2-(4'-Methoxy-biphenyl-4-yloxymethyl)-thiazole-4-carboxylic acid was prepared using general procedure B from 4-chloro-4'-hydroxybiphenyl (available from TCI America, Portland, Oreg.) and 2-bromomethyl-thiazole-4-carboxylic acid ethyl ester (Intermediate 3). Yield: 60 mg. Mass spectrum (ES) MH+=342.

Example 29

2-(Biphenyl-4-yloxymethyl)-thiazole-4-carboxylic acid

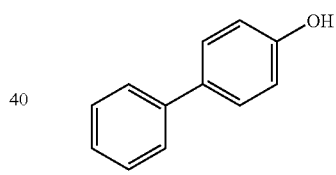

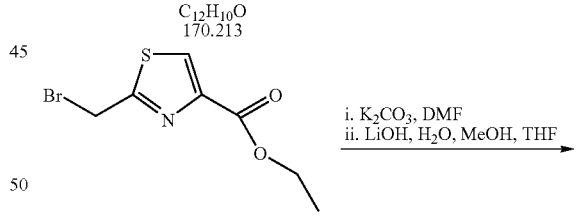

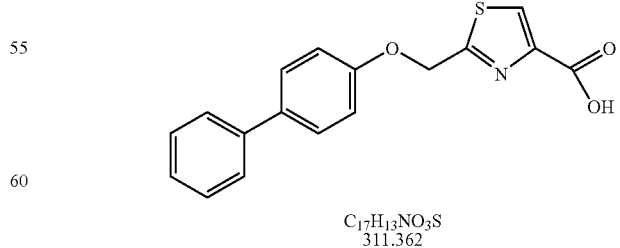

2-(Biphenyl-A-yloxymethyl)-thiazole-4-carboxylic acid was prepared using general procedure B from 4-phenylphenol (available from Aldrich, Milwaukee, Wis.) and 2-bromomethyl-thiazole-4-carboxylic acid ethyl ester (Intermediate 3). Yield: 56 mg. Mass spectrum (ES) MH+=312.

Example 30

4-(4'-Chloro-biphenyl-4-yloxymethyl)-thiazole-2-carboxylic acid

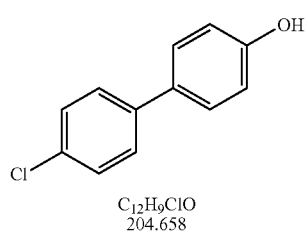

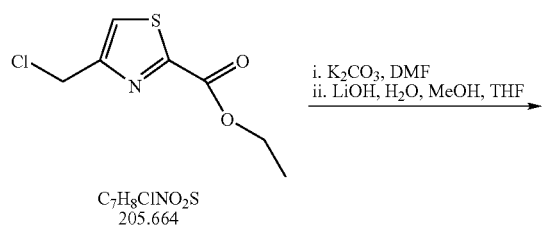

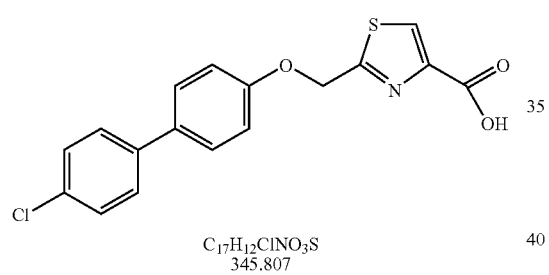

4-(4'-Chloro-biphenyl-4-yloxymethyl)-thiazole-2-carboxylic acid was prepared using general procedure B from 4-chloro-4'-hydroxybiphenyl (available from TCI America, Portland, Oreg.) and 4-chloromethyl-thiazole-2-carboxylic acid ethyl ester (Intermediate 4). Yield: 71 mg. Mass spectrum (ES) MH+=346.

Example 31

4-(Biphenyl-4-yloxymethyl)-thiazole-2-carboxylic acid

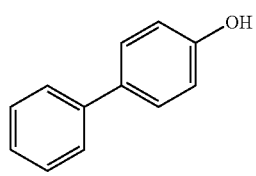

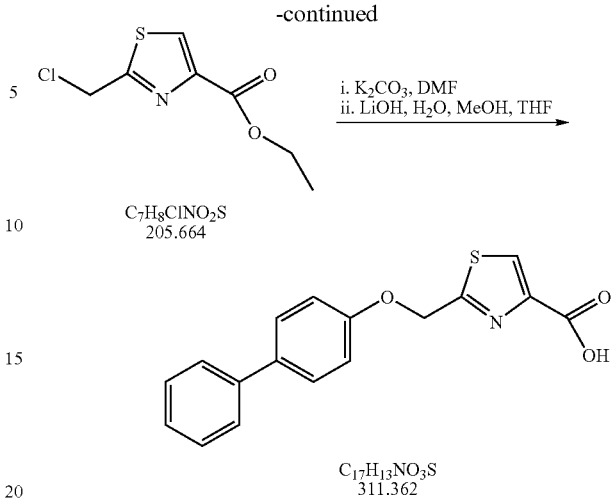

4-(Biphenyl-4-yloxymethyl)-thiazole-2-carboxylic acid was prepared using general procedure B from 4-phenylphenol (available from Aldrich, Milwaukee, Wis.) and 4-chloromethyl-thiazole-2-carboxylic acid ethyl ester (Intermediate 4). Yield: 54 mg. Mass spectrum (ES) M-OH=294

Example 32

1-[5-(Biphenyl-4-yloxymethyl)-furan-2-carbonyl]-D-pyrrolidine-2-carboxylic acid

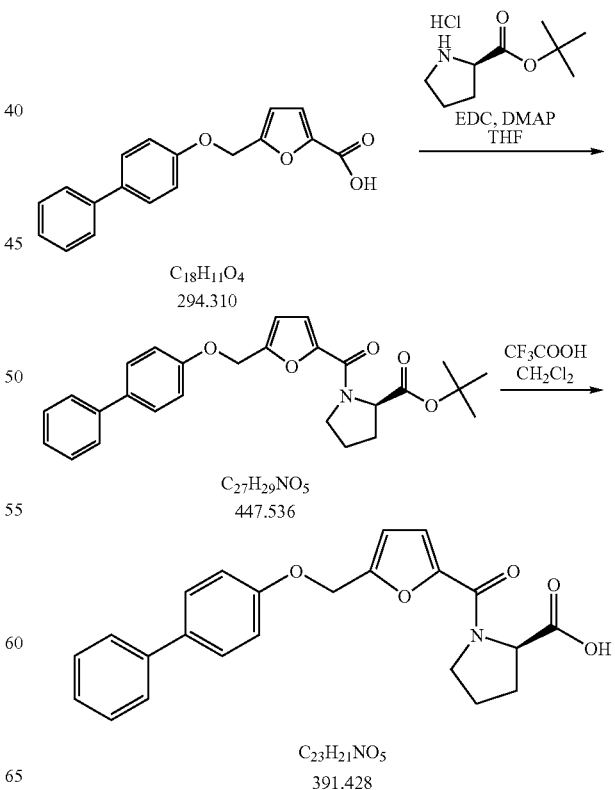

Step 1: 1-[5-(Biphenyl-4-yloxymethyl)-furan-2-carbonyl]-D-pyrrolidine-2-carboxylic acid methyl ester A solution of 5-(biphenyl-4-yloxymethyl)-furan-2-carboxylic acid (of Intermediate 8; 0.134 g, 0.46 mmol), D-proline tert-butyl ester hydrochloride (Bachem; 0.22 g, 1.1 mmol), 1-ethyl-3-(3-dimethylaminopropyl)-carbodiimide hydrochloride (Avocado; 0.18 g, 0.95 mmol), and N,N-dimethylaminopyridine (0.166 g, 1.36 mmol) in tetrahydrofuran (10 mL) was stirred at room temperature for 16 h. The solvents were evaporated under reduced pressure, and water and ethyl acetate were added. The aqueous phase was extracted three times with ethyl acetate, and the combined organic layers were dried (sodium sulfate), filtered, evaporated, and purified using a Biotage Flash 40 purification system, eluting with methylene chloride/acetone 9:1, to give 5-(biphenyl-4-yloxymethyl)-furan-2-carbonyl]-D-pyrrolidine-2-carboxylic acid tert-butyl ester as a white solid (0.115 g, 56%).

Step 2: 1-[5-(Biphenyl-4-yloxymethyl)-furan-2-carbonyl]-D-pyrrolidine-2-carboxylic acid Trifluoroacetic acid (1 mL) was added to a solution of 5-(biphenyl-4-yloxymethyl)-furan-2-carbonyl]-D-pyrrolidine-2-carboxylic acid tert-butyl ester (0.115 g, 0.26 mmol) in dichloromethane (4 mL) at 0° C. The solution was allowed to warm to room temperature and stir overnight. The solvents were evaporated under reduced pressure and ethyl acetate was added. Aqueous sodium hydrogen carbonate was added carefully, the layers were separated and the organic layer was discarded. The aqueous layer was acidified to pH 2 with 1 M HCl and the resulting mixture was extracted three times with ethyl acetate. The organic layers were combined, dried (sodium sulfate), filtered, and evaporated. The residue was triturated with ether, and the solid was filtered to give 5-(biphenyl-4-yloxymethyl)-furan-2-carbonyl]-D-pyrrolidine-2-carboxylic acid (64 mg, 64%) as a white solid.

Example 33

(rac)-1-[5-(Biphenyl-4-yloxymethyl)-furan-2-carbonyl]-piperidine-2-carboxylic acid

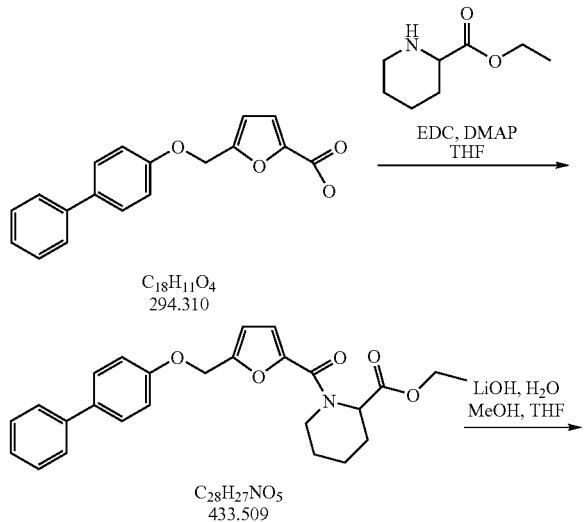

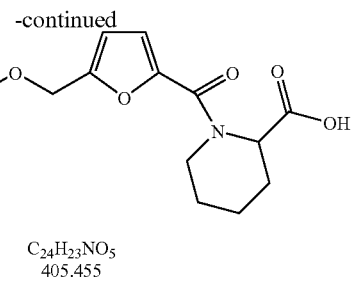

$C_{24}H_{23}NO_5$
405.455

Step 1: (rac)-1-[5-(Biphenyl-4-yloxymethyl)-furan-2-carbonyl]-piperidine-2-carboxylic acid ethyl ester A solution of 5-(biphenyl-4-yloxymethyl)-furan-2-carboxylic acid (of Intermediate 8; 0.098 g, 0.33 mmol), ethyl pipecolinate (Aldrich-0.139 g 0.88 mmol), 1-ethyl-3-(3-dimethylaminopropyl)-carbodiimide hydrochloride (Avocado; 0.13 g, 0.68 mmol), and N,N-dimethylaminopyridine (0.083 g, 0.68 mmol) in tetrahydrofuran (10 mL) was stirred at room temperature for 16 h. The solvents were evaporated under reduced pressure, and water and ethyl acetate were added. The aqueous phase was extracted three times with ethyl acetate, and the combined organic layers were dried (sodium sulfate) filtered, evaporated, and purified using a Biotage Flash 40 purification system, eluting with methylene chloride/acetone 9:1, to give (rac)-1-[5-(biphenyl-4-yloxymethyl)-furan-2-carbonyl]-piperidine-2-carboxylic acid ethyl ester as a colorless oil (0.085 g, 59%).

Step 2: (rac)-1-[5-(Biphenyl-4-yloxymethyl)-furan-2-carbonyl]-piperidine-2-carboxylic acid A solution of lithium hydroxide monohydrate (0.027 g 0.64 mmol) in water (1 mL) was added to a solution of (rac)-1-[5-(biphenyl-4-yloxymethyl)-furan-2-carbonyl]-piperidine-2-carboxylic acid ethyl ester (0.085 g, 0.2 mmol) in tetrahydrofuran (3 mL) and methanol (1 mL). The mixture was stirred overnight at room temperature and then the solvents were evaporated under reduced pressure. Water and ethyl acetate were added, and the mixture was acidified to pH 2 with 1 M HCl and the mixture was extracted three times with ethyl acetate. The combined organic layers were dried (sodium sulfate), filtered and evaporated. The residue was triturated with ether. The ether and dissolved impurities were removed by Pasteur pipette to give (rac)-1-[5-(biphenyl-4-yloxymethyl)-furan-2-carbonyl]-piperidine-2-carboxylic acid (66 mg, 83%) as a white solid.

Example 34

1-{[5-(Biphenyl-4-yloxymethyl)-furan-2-carbonyl]-amino}-cyclopentane carboxylic acid

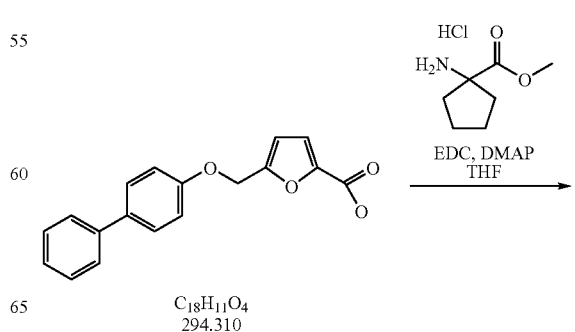

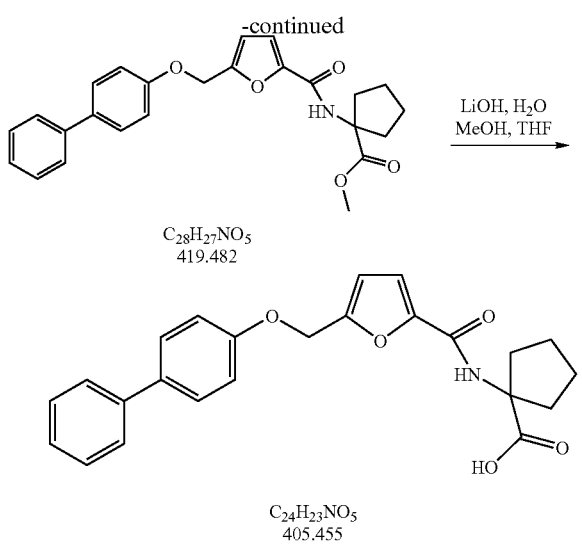

Step 1: 1-{[5-(Biphenyl-4-yloxymethyl)-furan-2-carbonyl]-amino}-cyclopentane carboxylic acid methyl ester Acetyl chloride (1 mL) was added to a cooled solution of methanol (10 mL) and the solution was allowed to warm to room temperature. Cycloleucine (Aldrich; 0.3 g, 2.3 mmol) was added and the solution was allowed to stir overnight at room temperature. The solvent was then evaporated to give cycloleucine methyl ester hydrochloride as an off-white solid which was then combined with 5-(biphenyl-4-yloxymethyl)-furan-2-carboxylic acid (of Intermediate 8; 0.085 g, 0.29 mmol), 1-ethyl-3-(3-dimethylaminopropyl)-carbodiimide hydrochloride (Avocado; 0.128 g, 0.67 mmol), and N,N-dimethylaminopyridine (0.16 g, 1.3 mmol) in tetrahydrofuran (5 mL). The reaction mixture was stirred at room temperature for 16 h. The solvents were evaporated under reduced pressure, and water and ethyl acetate were added. The aqueous phase was extracted three times with ethyl acetate, and the combined organic layers were dried (sodium sulfate), filtered, evaporated, and purified using a Biotage Flash 40 purification system, eluting with methylene chloride/acetone 9:1, to give 1-{[5-(biphenyl-4-yloxymethyl)-furan-2-carbonyl]-amino}-cyclopentanecarboxylic acid methyl ester as a colorless oil (0.085 g, 59%).

Step 2: 1-{[5-(Biphenyl-4-yloxymethyl)-furan-2-carbonyl]-amino}-cyclopentane carboxylic acid A solution of lithium hydroxide monohydrate (0.085 g, 2.0 mmol) in water (1 mL) was added to a solution of 1-{[5-(biphenyl-4-yloxymethyl)-furan-2-carbonyl]-amino}-cyclopentanecarboxylic acid methyl ester (0.092 g 0.22 mmol) in tetrahydrofuran (3 mL) and methanol (1 mL). The mixture was stirred overnight at room temperature and then the solvents were evaporated under reduced pressure. 0.5 M NaOH was added and the solution was extracted with ether. The aqueous layer was acidified with 1 M HCl and the mixture was extracted three times with ethyl acetate. The combined organic layers were dried (sodium sulfate), filtered, and evaporated to give 1-{[5-(biphenyl-4-yloxymethyl)-furan-2-carbonyl]-amino}-cyclopentanecarboxylic acid (61 mg, 69%) as a white solid.

Glycogen Synthase (GS) Assay

The following tests were carried out in order to determine the activity of the compounds of formula (I).

Twelve µl per well of substrate solution containing glycogen (4.32 mg/ml), 21.6 mM UDP-glucose, 21.6 mM phospho(enol)pyruvate and 2.7 mM NADH in 30 mM glycylglycine, pH 7.3 buffer was added into a polystyrene 384-well assay plate (BD Biosciences). Compound solution (8 µl/well) at various concentrations (0-57 µM) in 30 mM glycylglycine, pH 7.3, 40 mM KCl, 20 mM MgCl2 plus 9.2% DMSO were added to the assay plate (columns 5-24). Enzyme solution (12 µl/well) containing glycogen synthase (16.88 µg/ml), pyruvate kinase (0.27 mg/ml), lactate dehydrogenase (0.27 mg/ml) in 50 mM Tris-HCl pH 8.0, 27 mM DTT and bovine serum albumin (BSA, 0.2 mg/ml) was added to the assay plate (columns 3-24). As a blank control enzyme solution without glycogen synthase was added into the top half wells of columns 1-2. To the bottom half wells of columns 1-2 were added a known activator, glucose 6-phosphate (18.9 mM) in addition to the enzyme solution. The reaction mixture was incubated at 37° C. The assay plate was then read for absorbance at 340 nm on a Tecan Ultra reader every 3 minutes up to a total of 30 minutes.

The enzyme activity (with or without compound) was calculated by the reaction rate and represented by the optical density change (ΔOD) per minute. Percent stimulation of glycogen synthase activity by a compound at various concentrations was calculated by the following formula:

% stimulation=100*$Rs/Rt$, where Rs is the reaction rate of the enzyme in the presence of compound and Rt is the reaction rate of the enzyme in the absence of compound.

SC2.0 is defined as the compound concentration that is needed to stimulate 200% of the enzyme activity.

It should be understood of course, that the foregoing relates to preferred embodiments of the invention and that modifications may be made without departing from the spirit and scope of the invention as set forth in the following claims.

What is claimed is:

1. A compound of formula (I)

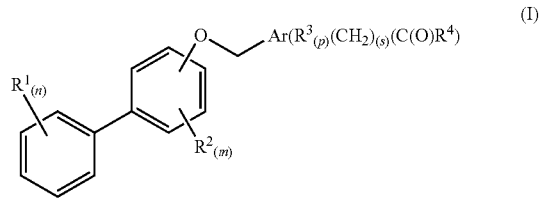

wherein
  Ar is a pyridinyl ring;
  $R^1$, $R^2$ and $R^3$ are independently selected from the group consisting of lower alkyl, lower alkoxy, trifluoromethyl, halogen, hydroxy, amino, alkylamino, dialkylamino, cyano and nitro;
  $R^4$ is hydroxy or an amino acid attached through a nitrogen atom of the amino acid;
  n is 0, 1, 2, 3, 4 or 5;
  m is 0, 1, 2, 3 or 4;
  p is 0, 1 or 2, and
  s is 0, 1 or 2 or a pharmaceutically acceptable salt thereof.

2. The compound of claim 1, wherein $R^1$, $R^2$ and $R^3$ are hydrogen atoms.

3. The compound of claim 1, wherein n=1 and $R^1$ is selected from the group consisting of a methyl group, a methoxy group, a halogen and a nitro group.

4. The compound of claim 3, wherein the halogen is chlorine or bromine.

5. The compound of claim 1, wherein m=1 and $R^2$ is a chlorine atom.

6. The compound of claim 1, wherein p and s=0.

7. The compound of claim 1, wherein $R^4$ is a hydroxyl group.

8. The compound of claim 1, wherein $R^4$ is proline, attached to the compound through its nitrogen atom.

9. The compound of claim 1, wherein the compound is selected from the group consisting of
6-(2'-Nitro-biphenyl-4-yloxymethyl)-pyridine-2-carboxylic acid; and
6-(Biphenyl-4-yloxymethyl)-pyridine-2-carboxylic acid.

10. A pharmaceutical composition comprising a compound of formula (1a)

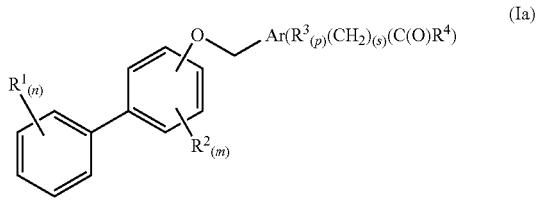

(Ia)

wherein
Ar is a pyridinyl ring;
$R^1$, $R^2$ and $R^3$ are independently selected from the group consisting of lower alkyl, lower alkoxy, trifluoromethyl, halogen, hydroxy, amino, alkylamino, dialkylamino, cyano and nitro;
$R^4$ is hydroxy or an amino acid attached through a nitrogen atom of the amino acid;
n is 0, 1, 2, 3, 4 or 5;
m is 0, 1, 2, 3 or 4;
p is 0, 1 or 2, and
s is 0, 1 or 2
or a pharmaceutically acceptable salt thereof, and a pharmaceutically acceptable carrier or excipient.

11. The pharmaceutical composition of claim 10, wherein $R^1$, $R^2$ and $R^3$ are hydrogen atoms.

12. The pharmaceutical composition of claim 10, wherein n=1 and $R^1$ is selected from the group consisting of a methyl group, a methoxy group, a halogen and a nitro group.

13. The pharmaceutical composition of claim 10, wherein the halogen is chlorine or bromine.

14. The pharmaceutical composition of claim 10, wherein m=1 and $R^2$ is a chlorine atom.

15. The pharmaceutical composition of claim 10, wherein p and s=0.

16. The pharmaceutical composition of claim 10, wherein $R^4$ is a hydroxyl group.

17. The pharmaceutical composition of claim 10, wherein $R^4$ is proline, attached to the compound through its nitrogen atom.

18. The pharmaceutical composition of claim 10, wherein the compound of Ia is selected from the group consisting of
6-(2'-Nitro-biphenyl-4-yloxymethyl)-pyridine-2-carboxylic acid; and
6-(Biphenyl-4-yloxymethyl)-pyridine-2-carboxylic acid.

* * * * *